(12) United States Patent
Steyaert et al.

(10) Patent No.: US 11,479,791 B2
(45) Date of Patent: *Oct. 25, 2022

(54) TOOLS AND METHODS FOR EXPRESSION OF MEMBRANE PROTEINS

(71) Applicants: VIB VZW, Ghent (BE); Vrije Universiteit Brussel, Brussels (BE); Universiteit Gent, Ghent (BE)

(72) Inventors: Jan Steyaert, Beersel (BE); Nico L. M. Callewaert, Nevele (BE); Toon Laeremans, Dworp (BE); Els Pardon, Wezemaal (BE); Kristof Vandewalle, Tielt (BE); Katrien Claes, Baasrode (BE)

( * ) Notice: Subject to any disclaimer, the term of this patent is extended or adjusted under 35 U.S.C. 154(b) by 307 days.

This patent is subject to a terminal disclaimer.

(21) Appl. No.: 15/894,531

(22) Filed: Feb. 12, 2018

(65) Prior Publication Data

US 2018/0237530 A1 Aug. 23, 2018

Related U.S. Application Data

(63) Continuation of application No. 14/373,329, filed as application No. PCT/EP2013/051041 on Jan. 21, 2013, now Pat. No. 9,890,217.

(60) Provisional application No. 61/588,523, filed on Jan. 19, 2012.

(30) Foreign Application Priority Data

Jan. 19, 2012 (EP) .................................... 12151814

(51) Int. Cl.
| | |
|---|---|
| *C12N 5/10* | (2006.01) |
| *C12N 15/85* | (2006.01) |
| *C07K 14/705* | (2006.01) |
| *C07K 14/72* | (2006.01) |
| *C07K 14/715* | (2006.01) |
| *C07K 16/28* | (2006.01) |
| *C12N 15/81* | (2006.01) |
| *G01N 33/50* | (2006.01) |
| *G01N 33/68* | (2006.01) |

(52) U.S. Cl.
CPC ............ *C12N 15/85* (2013.01); *C07K 14/705* (2013.01); *C07K 14/7158* (2013.01); *C07K 14/723* (2013.01); *C07K 16/2866* (2013.01); *C12N 15/815* (2013.01); *G01N 33/5041* (2013.01); *G01N 33/6863* (2013.01); *C07K 2317/569* (2013.01); *G01N 2333/7158* (2013.01); *G01N 2500/02* (2013.01); *G01N 2500/10* (2013.01); *G01N 2500/20* (2013.01)

(58) Field of Classification Search
None
See application file for complete search history.

(56) References Cited

U.S. PATENT DOCUMENTS

| | | | |
|---|---|---|---|
| 5,721,121 | A | 2/1998 | Etcheverry et al. |
| 6,730,499 | B1 | 5/2004 | Cregg |
| 2004/0029228 | A1 | 2/2004 | Presnell et al. |
| 2005/0106222 | A1 | 5/2005 | Ailor et al. |
| 2007/0048847 | A1 | 3/2007 | Presnell et al. |
| 2007/0122879 | A1 | 5/2007 | Presnell et al. |
| 2007/0134727 | A1 | 6/2007 | Presnell et al. |
| 2007/0264685 | A1 | 11/2007 | Presnell et al. |
| 2010/0160217 | A1 | 6/2010 | Williams et al. |
| 2011/0171627 | A1 | 7/2011 | Presnell et al. |
| 2012/0053321 | A1 | 3/2012 | Xu et al. |

FOREIGN PATENT DOCUMENTS

| | | |
|---|---|---|
| EP | 549062 A2 | 3/1999 |
| WO | 9937681 A2 | 7/1999 |
| WO | 0043507 A1 | 7/2000 |
| WO | 0190190 A2 | 11/2001 |
| WO | 0200879 A2 | 1/2002 |
| WO | 0248187 A2 | 6/2002 |
| WO | 02085945 A2 | 10/2002 |
| WO | 03025020 A1 | 3/2003 |
| WO | 03035694 A2 | 5/2003 |
| WO | 2004049794 A2 | 6/2004 |
| WO | 2004111194 A2 | 12/2004 |
| WO | 2006119497 A2 | 11/2006 |
| WO | 2010015722 A1 | 2/2010 |
| WO | 2010066740 A1 | 6/2010 |
| WO | 2010135678 A1 | 11/2010 |
| WO | 2011157761 A1 | 12/2011 |
| WO | 2013107905 A1 | 7/2013 |

OTHER PUBLICATIONS

PCT International Search Report and Written Opinion PCT/EP2013/051041, dated Jun. 21, 2013.
Rasmussen et al., Structure of a nanobody—stabilized active state of the beta 2 adrenoceptor, Nature, Jan. 13, 2011, pp. 175-180, vol. 469, No. 7329, Nature Publishing Group, United Kingdom.
Steyaert et al., Nanobody stabilization of G protein-coupled receptor conformational states, Current Opinion in Structural Biology, Jul. 21, 2011, pp. 567-572, vol. 21, No. 4.
PCT International Search Report, PCT/EP2013/107905, dated Jun. 21, 2013.
Junge et al., Large-scale production of functional membrane proteins, Cell. Mol. Life Sci., 2008, pp. 1729-1755, vol. 65.
Katzen et al., Membrane protein expression: no cells required, Trends in Biotechnology, Cell Press, 2009, pp. 455-460, vol. 27, No. 8.
Lu et al., Structural Studies of G Protein-Coupled Receptors, IUBMB Life, Nov. 2016, pp. 894-903, vol. 68, No. 11.

(Continued)

*Primary Examiner* — Michael D Pak
(74) *Attorney, Agent, or Firm* — Patent Law Works LLP

(57) ABSTRACT

The disclosure relates cells or cellular systems that express both a membrane protein and a binding domain directed to the membrane protein. Also, methods are provided that use such cells or cellular systems to produce higher amounts of the membrane proteins. Further, the cells or cellular systems can be used as tools for the structural and functional characterization of membrane proteins, as well as for screening and drug discovery efforts targeting membrane proteins.

15 Claims, 9 Drawing Sheets

Specification includes a Sequence Listing.

(56) References Cited

OTHER PUBLICATIONS

Wagner et al., Rationalizing membrane protein overexpression, Trends in Biotechnology, 2006, pp. 364-371, vol. 24, No. 8.
Carpenter, Byron, Current applications of mini G proteins to study the structure and function of G protein-coupled receptors, AIMS Bioengineering, Oct. 17, 2018, vol. 5(4): pp. 209-225, http://www.aimspress.com/journal/Bioengineering.
Nehme, Rony et al., Mini-G proteins: Novel tools for studying GPCRs in their active conformation, PLOS One, Apr. 20, 2017, vol. 12(4): e0175642. 26 pgs. https://doi.org/10.1371/journal.pone.0175642.

SEQUENCE LISTING

<160> NUMBER OF SEQ ID NOS: 32

<210> SEQ ID NO 1
<211> LENGTH: 129
<212> TYPE: PRT
<213> ORGANISM: Lama glama

<400> SEQUENCE: 1

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Thr Ser Gly Gly Ser Thr Asn Tyr Ala Asp Ser Val Lys
    50                  55                  60

Gly Arg Phe Thr Ile Ser Arg Asp Asn Ala Glu Asn Thr Val Tyr Leu
65                  70                  75                  80

Gln Met Asn Asn Leu Lys Pro Glu Asp Thr Ala Val Tyr Ser Cys Asn
                85                  90                  95

Ala Glu Gly Thr Ser Gly Ser Ser Arg Tyr Arg Arg Arg Tyr Glu Tyr
            100                 105                 110
```

Trp Gly Lys Gly Thr Gln Val Thr Val Ser Ser His His His His
          115                 120                 125

His

<210> SEQ ID NO 2
<211> LENGTH: 126
<212> TYPE: PRT
<213> ORGANISM: Lama glama

<400> SEQUENCE: 2

Gln Val Gln Leu Gln Glu Ser Gly Gly Gly Leu Val Arg Thr Gly Gly
1               5                   10                  15

Ser Leu Arg Leu Ser Cys Ala Gly Ser Gly Ser Phe Phe Ser Ile Asn
            20                  25                  30

Pro Met Gly Trp Tyr Arg Gln Ala Pro Gly Gln Gln Arg Glu Leu Val
        35                  40                  45

Ala Thr Ile Thr Gly Ser Gly Ser Thr Asn Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Ala Gly Tyr Phe Asp Arg Ile Gly Arg Arg Tyr Asp Arg Trp Gly Gln
            100                 105                 110

Gly Thr Gln Val Thr Val Ser Ser His His His His His His
        115                 120                 125

<210> SEQ ID NO 3
<211> LENGTH: 130
<212> TYPE: PRT
<213> ORGANISM: Lama glama

<400> SEQUENCE: 3

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Asn Ser Gly Gly Arg Ser Ala Asn Tyr Ala Asp Ser Val
    50                  55                  60

Lys Gly Arg Leu Thr Ile Ser Arg Asp Asn Ala Lys Asn Thr Leu His
65                  70                  75                  80

Leu Gln Met Asn Ser Leu Lys Pro Glu Asp Thr Ala Leu Tyr Tyr Cys
                85                  90                  95

Ala Arg Pro Arg Ser Val Ser Arg Asn Tyr Val Pro Leu Gly Tyr Asp
            100                 105                 110

Tyr Leu Gly Gln Gly Thr Gln Val Thr Val Ser Ser His His His His
        115                 120                 125

His His
    130

<210> SEQ ID NO 4
<211> LENGTH: 125
<212> TYPE: PRT
<213> ORGANISM: Lama glama

<400> SEQUENCE: 4

```
Gln Val Gln Leu Gln Glu Ser Gly Gly Gly Leu Val Gln Ala Gly
1               5                   10                  15

Ser Leu Arg Leu Ser Cys Ala Ala Ser Gly Ser Thr Ser Gly Ile Ile
            20                  25                  30

Ala Met Gly Trp Tyr Arg Gln Ala Pro Gly Lys Gln Arg Glu Leu Val
        35                  40                  45

Ala Arg Ile Ser Ser Gly Ser Ser Thr Asn Tyr Ala Asp Ser Val Lys
        50                  55                  60

Gly Arg Phe Thr Val Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Val Arg Arg Gly Tyr Arg Asn Asp Tyr Asn Ser Trp Gly Gln Gly
            100                 105                 110

Thr Gln Val Thr Val Ser Ser His His His His His
        115                 120                 125
```

<210> SEQ ID NO 5
<211> LENGTH: 130
<212> TYPE: PRT
<213> ORGANISM: Lama glama

<400> SEQUENCE: 5

```
Met Glu Val Gln Leu Gln Glu Ser Gly Gly Gly Leu Val Gln Ala Gly
1               5                   10                  15

Gly Ser Leu Arg Leu Ser Cys Ala Ala Ser Gly Ser Ile Phe Ser Ile
            20                  25                  30

Asn Thr Met Gly Trp Tyr Arg Gln Ala Pro Gly Lys Gln Arg Glu Leu
        35                  40                  45

Val Ala Ala Ile His Ser Gly Ser Thr Asn Tyr Ala Asn Ser Val
        50                  55                  60

Lys Gly Arg Phe Thr Ile Ser Arg Asp Asn Ala Ala Asn Thr Val Tyr
65                  70                  75                  80

Leu Gln Met Asn Ser Leu Lys Pro Glu Asp Thr Ala Val Tyr Tyr Cys
                85                  90                  95

Asn Val Lys Asp Tyr Gly Ala Val Leu Tyr Glu Tyr Asp Tyr Trp Gly
            100                 105                 110

Gln Gly Thr Gln Val Thr Val Ser Ser Ala Ala Ala His His His
        115                 120                 125

His His
    130
```

<210> SEQ ID NO 6
<211> LENGTH: 136
<212> TYPE: PRT
<213> ORGANISM: Lama glama

<400> SEQUENCE: 6

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Arg Ser Ile Val
            20                  25                  30

Ser Met Ala Trp Tyr Arg Gln Ala Pro Gly Lys Gln Arg Glu Leu Val
        35                  40                  45

Ala Ser Ser Asn Ser Gly Gly Ser Thr Asn Tyr Ala Asp Ser Val Lys
        50                  55                  60
```

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Trp Cys Asn
                 85                  90                  95

Val Gln Asn Arg Leu Pro Gly Phe Asp Ala Phe Ser Gly Arg Ser Ile
            100                 105                 110

Ala Glu Thr Tyr Trp Gly Gln Gly Thr Gln Val Thr Val Ser Ser Ala
        115                 120                 125

Ala Ala His His His His His His
        130                 135

<210> SEQ ID NO 7
<211> LENGTH: 8
<212> TYPE: PRT
<213> ORGANISM: Lama glama

<400> SEQUENCE: 7

Gly Ser Ile Phe Ser Ile Asn Ala
 1               5

<210> SEQ ID NO 8
<211> LENGTH: 16
<212> TYPE: PRT
<213> ORGANISM: Lama glama

<400> SEQUENCE: 8

Ala Ala Ile Thr Ser Gly Gly Ser Thr Asn Tyr Ala Asp Ser Val Lys
 1               5                  10                  15

<210> SEQ ID NO 9
<211> LENGTH: 17
<212> TYPE: PRT
<213> ORGANISM: Lama glama

<400> SEQUENCE: 9

Asn Ala Glu Gly Thr Ser Gly Ser Ser Arg Tyr Arg Arg Arg Tyr Glu
 1               5                  10                  15

Tyr

<210> SEQ ID NO 10
<211> LENGTH: 8
<212> TYPE: PRT
<213> ORGANISM: Lama glama

<400> SEQUENCE: 10

Gly Ser Phe Phe Ser Ile Asn Pro
 1               5

<210> SEQ ID NO 11
<211> LENGTH: 16
<212> TYPE: PRT
<213> ORGANISM: Lama glama

<400> SEQUENCE: 11

Ala Thr Ile Thr Gly Ser Gly Ser Thr Asn Tyr Ala Asp Ser Val Lys
 1               5                  10                  15

<210> SEQ ID NO 12
<211> LENGTH: 14
<212> TYPE: PRT
<213> ORGANISM: Lama glama
```

```
<400> SEQUENCE: 12

Asn Ala Gly Tyr Phe Asp Arg Ile Gly Arg Arg Tyr Asp Arg
1               5                   10

<210> SEQ ID NO 13
<211> LENGTH: 8
<212> TYPE: PRT
<213> ORGANISM: Lama glama

<400> SEQUENCE: 13

Gly Phe Thr Phe Ser Ser Tyr Ala
1               5

<210> SEQ ID NO 14
<211> LENGTH: 15
<212> TYPE: PRT
<213> ORGANISM: Lama glama

<400> SEQUENCE: 14

Ile Asn Ser Gly Gly Arg Ser Ala Asn Tyr Ala Asp Ser Val Lys
1               5                   10                  15

<210> SEQ ID NO 15
<211> LENGTH: 17
<212> TYPE: PRT
<213> ORGANISM: Lama glama

<400> SEQUENCE: 15

Ala Arg Pro Arg Ser Val Ser Arg Asn Tyr Val Pro Leu Gly Tyr Asp
1               5                   10                  15

Tyr

<210> SEQ ID NO 16
<211> LENGTH: 8
<212> TYPE: PRT
<213> ORGANISM: Lama glama

<400> SEQUENCE: 16

Gly Ser Thr Ser Gly Ile Ile Ala
1               5

<210> SEQ ID NO 17
<211> LENGTH: 16
<212> TYPE: PRT
<213> ORGANISM: Lama glama

<400> SEQUENCE: 17

Ala Arg Ile Ser Ser Gly Ser Ser Thr Asn Tyr Ala Asp Ser Val Lys
1               5                   10                  15

<210> SEQ ID NO 18
<211> LENGTH: 13
<212> TYPE: PRT
<213> ORGANISM: Lama glama

<400> SEQUENCE: 18

Asn Ala Val Arg Arg Gly Tyr Arg Asn Asp Tyr Asn Ser
1               5                   10

<210> SEQ ID NO 19
<211> LENGTH: 387
<212> TYPE: DNA
<213> ORGANISM: Lama glama
```

```
<400> SEQUENCE: 19
caggtgcagc tgcaggagtc tgggggaggc ttggtgcagc ctgggggtc tctgagactc        60 tcctgtgcag cctctggaag catcttcagt atcaatgcca tgggctggta ccgccaggct      120
ccagggaagc agcgcgagtt ggtcgcagct attactagtg gtggtagcac aaactatgca      180
gactccgtaa agggccgatt caccatctcc agagacaacg ccgagaacac ggtgtatctg      240
caaatgaaca acctgaaacc tgaggacacg gccgtctatt catgtaacgc tgaaggaacg      300
tcgggtagta gccggtatcg ccgccggtat gagtactggg gcaaggggac ccaggtcacc      360
gtctcctcac accaccatca ccatcac                                           387

<210> SEQ ID NO 20
<211> LENGTH: 378
<212> TYPE: DNA
<213> ORGANISM: Lama glama

<400> SEQUENCE: 20
caggtgcagc tgcaggagtc tggaggaggc ttggtgcgca ctgggggtc tctgagactc        60 tcctgtgcag gctctggaag cttcttcagt atcaatccca tgggctggta ccgccaggct      120
ccagggcagc agcgcgagtt ggtcgcaact attactggta gtggtagcac aaactatgca      180
gactccgtga agggccgatt caccatctcc agagacaacg ccaagaacac actgtatctg      240
caaatgaaca gcctgaaacc tgaggacacg gccgtctatt actgtaatgc aggatatttc      300
gatcggattg gtcggcggta tgaccgctgg ggccagggga cccaggtcac cgtctcctca      360
caccaccatc accatcac                                                    378

<210> SEQ ID NO 21
<211> LENGTH: 393
<212> TYPE: DNA
<213> ORGANISM: Lama glama

<400> SEQUENCE: 21
caggtgcagc tgcaggagtc tggaggaggc ttggtgcagc ctgggggtc tctgagactc        60 tcctgtgcag cctctggatt caccttcagt agctatgcca tgagctgggt ccgccaggct      120
ccaggaaagg ggctcgagtg gtctcaact attaatagtg gtggtcgtag cgcaaactat      180
gcagactccg tgaagggccg actcaccatc tccagagaca acgccaagaa cacgctgcat      240
ctgcaaatga acagcctgaa acctgaggac acggccctgt attactgtgc gagaccccgt      300
agtgtaagtc gcaactatgt tccactcgga tacgactact ggggccaggg gacccaggtc      360
accgtctcct cacaccacca tcaccatcac tag                                    393

<210> SEQ ID NO 22
<211> LENGTH: 384
<212> TYPE: DNA
<213> ORGANISM: Lama glama

<400> SEQUENCE: 22
caggtgcagc tgcaggagtc tggaggaggc ttggtgcagg ctgggggtc tctgagactc        60 tcctgtgcag cctctggaag cacctccggt atcattgcca tgggctggta ccgccaggct      120
ccagggaagc agcgcgagtt ggtcgcacgt attagtagtg gtagtagtac aaactatgca      180
gactccgtga agggccgatt caccgtctcc agagacaacg ccaagaacac agtgtatctg      240
caaatgaaca gcctgaaacc tgaggacacg gccgtctatt actgtaatgc agtccgtcga      300
ggttaccgta acgactataa ctcctggggc caggggaccc aggtcaccgt ctcctcacac      360
```

```
caccatcacc atcactagac tagt                                          384
```

<210> SEQ ID NO 23
<211> LENGTH: 393
<212> TYPE: DNA
<213> ORGANISM: Lama glama

<400> SEQUENCE: 23

```
atggaggtgc agctgcagga gtctggggga ggcttggtgc aggctggggg gtctctgaga   60
ctctcctgtg cagcctctgg aagcatcttc agtatcaata ccatgggctg gtaccgccag  120
gctccaggga agcagcgcga gttggtcgca gctattcata gtggtggtag cacaaactat  180
gccaactccg tgaagggccg attcaccatc tccagagaca tgccgcgaa cacggtgtat   240
ctgcaaatga acagcctgaa acctgaggac acggccgtct attactgtaa tgtaaaggac  300
tacggggcgg tcctatatga gtatgactac tggggccagg ggacccaggt caccgtctcc  360
tcagcggccg cacatcatca tcaccatcac tag                                393
```

<210> SEQ ID NO 24
<211> LENGTH: 408
<212> TYPE: DNA
<213> ORGANISM: Lama glama

<400> SEQUENCE: 24

```
caggtgcagc tggtggagtc tgggggaggc ttggtgcagc tggggggtc tctgagactc    60
tcctgtgcag cctctggaag cttccgcagt atcgtgtcta tggcctggta ccgccaggct  120
ccagggaagc agcgcgagtt ggtcgcaagt tctaatagtg ggggcagcac aaattatgca  180
gactccgtga agggccgatt caccatctcc agagacaacg ccaagaacac ggtgtatctg  240
caaatgaaca gcctgaaacc tgaggacacg gccgtgtatt ggtgtaatgt ccaaaaccgc  300
ctcccgggat cgacgccctt tagtggcaga tctatagcgg agacctattg gggccagggg  360
acccaggtca ccgtctcctc agcggccgca catcatcatc accatcac                408
```

<210> SEQ ID NO 25
<211> LENGTH: 9
<212> TYPE: PRT
<213> ORGANISM: Artificial Sequence
<220> FEATURE:
<223> OTHER INFORMATION: C-terminal Rho1D4-tag

<400> SEQUENCE: 25

```
Thr Glu Thr Ser Gln Val Ala Pro Ala
1               5
```

<210> SEQ ID NO 26
<211> LENGTH: 43
<212> TYPE: DNA
<213> ORGANISM: Artificial Sequence
<220> FEATURE:
<223> OTHER INFORMATION: Primer

<400> SEQUENCE: 26

```
gaagaagggg tatctctcga gaaaaggcag gtgcagctgc agg                      43
```

<210> SEQ ID NO 27
<211> LENGTH: 40
<212> TYPE: DNA
<213> ORGANISM: Artificial Sequence
<220> FEATURE:
<223> OTHER INFORMATION: Primer

<400> SEQUENCE: 27
tcatgtctaa ggctaactag tctagtgatg gtgatggtgg                              40

<210> SEQ ID NO 28
<211> LENGTH: 21
<212> TYPE: DNA
<213> ORGANISM: Artificial Sequence
<220> FEATURE:
<223> OTHER INFORMATION: Primer

<400> SEQUENCE: 28
gactggttcc aattgacaag c                                                  21

<210> SEQ ID NO 29
<211> LENGTH: 21
<212> TYPE: DNA
<213> ORGANISM: Artificial Sequence
<220> FEATURE:
<223> OTHER INFORMATION: Primer

<400> SEQUENCE: 29
gcaaatggca ttctgacatc c                                                  21

<210> SEQ ID NO 30
<211> LENGTH: 36
<212> TYPE: DNA
<213> ORGANISM: Artificial Sequence
<220> FEATURE:
<223> OTHER INFORMATION: Primer

<400> SEQUENCE: 30
agtctgctcg agccaccatg gaggtgcagc tgcagg                                  36

<210> SEQ ID NO 31
<211> LENGTH: 65
<212> TYPE: DNA
<213> ORGANISM: Artificial Sequence
<220> FEATURE:
<223> OTHER INFORMATION: Primer

<400> SEQUENCE: 31
cagactagat ctctagtgat ggtgatgatg atgtgcggcc gctgaggaga cggtgacctg        60
ggtcc                                                                    65

<210> SEQ ID NO 32
<211> LENGTH: 456
<212> TYPE: PRT
<213> ORGANISM: Artificial Sequence
<220> FEATURE:
<223> OTHER INFORMATION: Construct of figure 4: Protein sequence of
      hCXCR4Rho1D4 fused to the alpha-mating factor of S. cerevisiae

<400> SEQUENCE: 32

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val

```
                65                  70                  75                  80
Ser Leu Glu Lys Arg Glu Ala Glu Ala Met Ser Ile Pro Leu Pro Leu
                        85                  90                  95

Leu Gln Ile Tyr Thr Ser Asp Asn Tyr Thr Glu Glu Met Gly Ser Gly
            100                 105                 110

Asp Tyr Asp Ser Met Lys Glu Pro Cys Phe Arg Glu Asn Ala Asn
            115                 120                 125

Phe Asn Lys Ile Phe Leu Pro Thr Ile Tyr Ser Ile Phe Leu Thr
    130                 135                 140

Gly Ile Val Gly Asn Gly Leu Val Ile Leu Val Met Gly Tyr Gln Lys
145                 150                 155                 160

Lys Leu Arg Ser Met Thr Asp Lys Tyr Arg Leu His Leu Ser Val Ala
                    165                 170                 175

Asp Leu Leu Phe Val Ile Thr Leu Pro Phe Trp Ala Val Asp Ala Val
                180                 185                 190

Ala Asn Trp Tyr Phe Gly Asn Phe Leu Cys Lys Ala Val His Val Ile
            195                 200                 205

Tyr Thr Val Asn Leu Tyr Ser Ser Val Leu Ile Leu Ala Phe Ile Ser
        210                 215                 220

Leu Asp Arg Tyr Leu Ala Ile Val His Ala Thr Asn Ser Gln Arg Pro
225                 230                 235                 240

Arg Lys Leu Leu Ala Glu Lys Val Val Tyr Val Gly Val Trp Ile Pro
                245                 250                 255

Ala Leu Leu Leu Thr Ile Pro Asp Phe Ile Phe Ala Asn Val Ser Glu
            260                 265                 270

Ala Asp Asp Arg Tyr Ile Cys Asp Arg Phe Tyr Pro Asn Asp Leu Trp
        275                 280                 285

Val Val Val Phe Gln Phe Gln His Ile Met Val Gly Leu Ile Leu Pro
    290                 295                 300

Gly Ile Val Ile Leu Ser Cys Tyr Cys Ile Ile Ile Ser Lys Leu Ser
305                 310                 315                 320

His Ser Lys Gly His Gln Lys Arg Lys Ala Leu Lys Thr Thr Val Ile
                325                 330                 335

Leu Ile Leu Ala Phe Phe Ala Cys Trp Leu Pro Tyr Tyr Ile Gly Ile
            340                 345                 350

Ser Ile Asp Ser Phe Ile Leu Leu Glu Ile Ile Lys Gln Gly Cys Glu
        355                 360                 365

Phe Glu Asn Thr Val His Lys Trp Ile Ser Ile Thr Glu Ala Leu Ala
    370                 375                 380

Phe Phe His Cys Cys Leu Asn Pro Ile Leu Tyr Ala Phe Leu Gly Ala
385                 390                 395                 400

Lys Phe Lys Thr Ser Ala Gln His Ala Leu Thr Ser Val Ser Arg Gly
                405                 410                 415

Ser Ser Leu Lys Ile Leu Ser Lys Gly Lys Arg Gly Gly His Ser Ser
            420                 425                 430

Val Ser Thr Glu Ser Glu Ser Ser Phe His Ser Ser Ala Gly Thr
        435                 440                 445

Glu Thr Ser Gln Val Ala Pro Ala
450                 455
```

TOOLS AND METHODS FOR EXPRESSION OF MEMBRANE PROTEINS

CROSS-REFERENCE TO RELATED APPLICATIONS

This application is a continuation of U.S. patent application Ser. No. 14/373,329, filed Jul. 18, 2014, which will issue as U.S. Pat. No. 9,890,217 on Feb. 13, 2018, which is a national phase entry under 35 U.S.C. § 371 of International Patent Application PCT/EP2013/051041, filed Jan. 21, 2013, designating the United States of America and published in English as International Patent Publication WO2013/107905 A1 on Jul. 25, 2013, which claims the benefit under Article 8 of the Patent Cooperation Treaty to European Application Serial No. 12151814.6, filed Jan. 19, 2012, and under 35 U.S.C. § 119(e) to U.S. Provisional Application Ser. No. 61/588,523, filed Jan. 19, 2012, the disclosure of each of which is hereby incorporated herein in its entirety by this reference.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

TECHNICAL FIELD

The disclosure relates to the field of protein expression technologies. More specifically, cells or cellular systems are provided that express both a membrane protein and a binding domain directed to the membrane protein. Also, methods are provided that use such cells or cellular systems to produce higher amounts of the membrane proteins. Further, the cells or cellular systems can be used as tools for the structural and functional characterization of membrane proteins, as well as for screening and drug discovery efforts targeting membrane proteins.

BACKGROUND

There has been increasing interest and progress in the field of membrane protein research over the last years. The high interest in membrane proteins is due to the fact that they play an important role in several biological processes such as ion transport, recognition of molecules, signal transduction, etc. G-protein coupled receptors (GPCRs) constitute the largest family of transmembrane proteins and play an important part in signal transduction by converting extracellular stimuli including light, smells, neurotransmitters and hormones, into intracellular signals. Currently, more than 30% of marketed medicines act on GPCRs, which are considered as attractive targets for new medicines. Structure-based drug discovery and high throughput screening (HTS) for novel compounds active on a receptor of interest have now become an integrated technology in pharmaceutical laboratories.

Although membrane proteins represent 20% to 30% of all genes in prokaryotes as well as in eukaryotes, only little is known about structure and function relationship of membrane proteins. This can be largely attributed to the low natural expression of membrane proteins, to their hydrophobic character, which complicates overexpression of functional membrane proteins, as well as to difficulties during their purification and crystallization. By way of example, only for seven GPCRs high-resolution structures have been characterized: rhodopsin, the β1 and β2 adrenergic receptors, the adenosine 2A receptor, and more recently the CXCR4 receptor, the dopamine D3 receptor and the histamine H1 receptor. Whereas rhodopsin was purified and subsequently crystallized from unmodified protein isolated from native tissue (a lone exception to the rule of low expression levels), these other GPCRs required expression in recombinant systems, stabilization of an inactive state by an inverse agonist/antagonist and biochemical modifications to stabilize the receptor protein (e.g., Rasmussen et al., 2007, Nature 450:383; Rosenbaum et al., 2007, Science, 318: 1266; Warne et al., 2008, Nature 454:486; Wu et al., 2010, Science 330:1066; Chien et al., 2010, Science 330:091; Shimamura et al., 2011, Nature 475: 65. Up till now, most unravelled structures have the third cytoplasmic loop replaced for the very stable bacteriophage T4 lysozyme. This fusion protein might however not represent the true natural conformation of the GPCR. Therefore, the structures need to be analyzed with great care when performing ligand screening and drug design. Besides that, evidence from functional and biophysical studies shows that GPCRs can exist in multiple functionally distinct conformational states (Kobilka and Deupi 2007, Trends Pharmacol Sciences 28:397). While this structural plasticity and dynamic behavior is essential for normal function, it contributes to their biochemical instability and difficulty in obtaining high-resolution crystal structures. Only recently it became possible to obtain structures of an active state of a GPCR, making use of stabilizing Nanobodies (Rasmussen et al., 2011, Nature 469: 175).

Most membrane proteins express at low levels in non-engineered eukaryotic cells. Eukaryotic membrane proteins have been successfully overexpressed in bacteria, yeast, mammalian cell lines and insect cells (reviewed in Freigassner et al., 2009, Microb Cell Fact. 8:69). However, expression levels are still rather low and for the majority of these receptors a 5- to 10-fold increase in expression level would lead to sufficient material for subsequent experiments, especially protein purification and characterization, structural and pharmacological studies. For example, expression of eukaryotic membrane proteins in prokaryotic systems mostly leads to poor expression levels. Besides, in many cases the protein ends up in denatured form in inclusion bodies and the necessity of complicated refolding processes has hampered the success. Expression in yeast is a valuable alternative for the expression of eukaryotic membrane proteins. Yeast cells are easy to handle, and can grow in fermentors to very high cell densities. Different techniques to increase the expression levels of the membrane protein have been used in yeast such as lowering the induction temperature, adding antagonist, DMSO or histidine to the induction medium (André et al., 2006, Protein Sci. 15:1115). Other approaches have been taken to enhance membrane protein surface expression in heterologous cells, including addition/deletion of receptor sequences, co-expression with interacting proteins, and treatment with pharmacological chaperones (reviewed in Dunham and Hall, 2009, Trends Biotechnol. 27:541). It remains a challenge, however, to significantly improve total yield, conformational stability and/or functionality of wild-type surface expressed membrane protein.

Thus, it would be advantageous to have alternative expression systems that permit higher heterologous expression of native membrane proteins in a particular conformation. This would greatly facilitate the whole trajectory of drug discovery efforts on membrane proteins as therapeutic targets.

SUMMARY OF THE INVENTION

The disclosure provides tools and methods for heterologous expression of membrane proteins which are of particular advantage. To illustrate this, without being limitative, the human CXCR4 (hCXCR4) GPCR was co-expressed with Nanobodies (Nbs) directed against hCXCR4 in the yeast strain P. pastoris. It was surprisingly found that hCXCR4-Nb co-expression results in an increase in expression of the membrane protein, as compared to hCXCR4 expression alone. In addition, because of the interaction between the GPCR and the Nb, the membrane protein can be directly purified from the co-expressing host cell using affinity-based purification methods. Furthermore, when a conformation-selective Nb is used, it is possible to purify the fraction of the membrane proteins that particularly resides in the conformation as stabilized by the Nb. Thus, using the tools and methods of the disclosure, the homogeneity of a membrane protein sample is increased, which is particularly useful, e.g., for subsequent crystallization, immunization or compound screening. The skilled artisan will understand that the above findings will generally be applicable for the co-expression of other type of membrane proteins and binding domains directed against these membrane proteins.

Accordingly, a first aspect of the disclosure relates to a host cell comprising a first exogenous nucleic acid sequence encoding a membrane protein and a second exogenous nucleic acid encoding a binding domain directed against the membrane protein, each under the control of a promoter. In a preferred embodiment, the promoter is an inducible promoter. In another preferred embodiment, the membrane protein and binding domain are co-expressed. In still another embodiment, the membrane protein and/or the binding domain are operably linked to a subcellular targeting sequence, such as an ER or Golgi localization signal or secretion signal.

According to particular embodiments, the membrane protein in any of the above-described host cells is a membrane receptor protein, such as a GPCR, or a membrane transport protein, such as an ion transporter.

A further embodiment of the disclosure relates to any of the above-described host cells wherein the binding domain specifically binds to an extracellular conformational epitope of the membrane protein.

Preferably, the binding domain in any of the above-described host cells is an immunoglobulin single variable domain comprising an amino acid sequence comprising 4 framework regions and 3 complementarity-determining regions, or any suitable fragment thereof. More preferably, the immunoglobulin single variable domain is a VHH.

In a particularly preferred embodiment of any of the above-described host cells, the immunoglobulin single variable domain stabilizes the membrane protein in a functional conformational state, such as an active or an inactive state.

The host cell, according to the disclosure, may be a eukaryotic host cell, such as a yeast cell, a mammalian cell, an insect cell. In particular, the yeast may be a *Pichia* strain, such as a *Pichia pastoris*, or a *Komagataella* strain, such as *Komagataella pastoris*, or a *Hansenula* strain, such as *Hansenula polymorpha*, or a *Yarrowia* strain, such as *Yarrowia lipolytica*, or a *Saccharomyces* strain, such as *Saccharomyces cerevisiae*, and wherein the filamentous fungi is an *Aspergillus* strain, such as *Aspergillus niger* or *Aspergillus nidulans*, or a *Penicillium* strain, such as *Penicillium citrinum* or *Penicillium chrysogenum*, or a *Hypocrea* strain, such as *Hypocrea jecorina*.

In addition, the host cell may be a glycoengineered host cell.

In another aspect, the disclosure also envisages cell cultures of any of the above-described host cells or membrane preparations derived of the host cells or cell cultures. Expression vectors comprising the first and/or the second exogenous nucleic acid sequence as comprised in the host cells according to the disclosure are also encompassed.

According to a further aspect, the disclosure relates to a method of enhancing the production of a membrane protein in a host cell comprising the steps of:
 a. Providing a host cell as described above,
 b. Culturing the host cell under conditions suitable for co-expressing the membrane protein and the binding domain directed against the membrane protein.

Also envisages is a method of enhancing the production of a membrane protein in a functional conformation in a host cell, the method comprising the steps of:
 a. Providing a host cell as described above,
 b. Culturing the host cell under conditions suitable for co-expressing the membrane protein and the binding domain directed against the membrane protein, in the presence of a conformation-selective ligand, such as an agonist, an antagonist, an inverse agonist.

The method may further comprise the step of isolating the membrane protein, the binding domain or the membrane protein in complex with the binding domain.

Finally, the disclosure also relates to the use of the host cells, or the cell cultures, or the membrane preparations, or the proteins isolated therefrom, all as described hereinbefore, for ligand characterization, drug screening, protein capturing and purification, immunization, biophysical studies, amongst others. Other applications will become clear from the description further herein.

BRIEF DESCRIPTION OF THE DRAWINGS

FIG. 3A: SDS-PAGE Coomassie Brilliant Blue detection of the four anti-hCXCR4 Nanobodies. M=All blue precision plus protein standards. FIG. 3B: immunoblot detection of the four anti-hCXCR4 Nanobodies. Mouse anti-His antibody and secondary goat anti-mouse (800 nm) DyLight antibody was used for the detection of the nanobodies on the Odyssey system.

FIG. 4A: Protein sequence of hCXCR4Rho1D4 fused to the alpha-mating factor of *S. cerevisiae*. Schematic overview of the pPIC92hCXCR4Rho1D4 expression vector, containing the hCXCR4Rho1D4 gene under control of the AOX1 promoter (SEQ ID NO:32). FIG. 4B: vector linearized with restriction enzyme StuI to facilitate targeted integration in the HIS4 locus of the *Pichia* genome.

FIG. 7A: Nanobody CA4140 and CA4142 both in the presence or absence of hCXCR4Rho1D4. FIG. 7B: Nanobody CA4143 and CA4500 both in the presence or absence of hCXCR4Rho1D4. M=All blue precision plus protein standards. Mouse anti-His antibody and secondary goat anti-mouse (800 nm) DyLight antibody was used for the detection of the nanobodies on the Odyssey system.

DETAILED DESCRIPTION OF THE INVENTION

Figure 1:
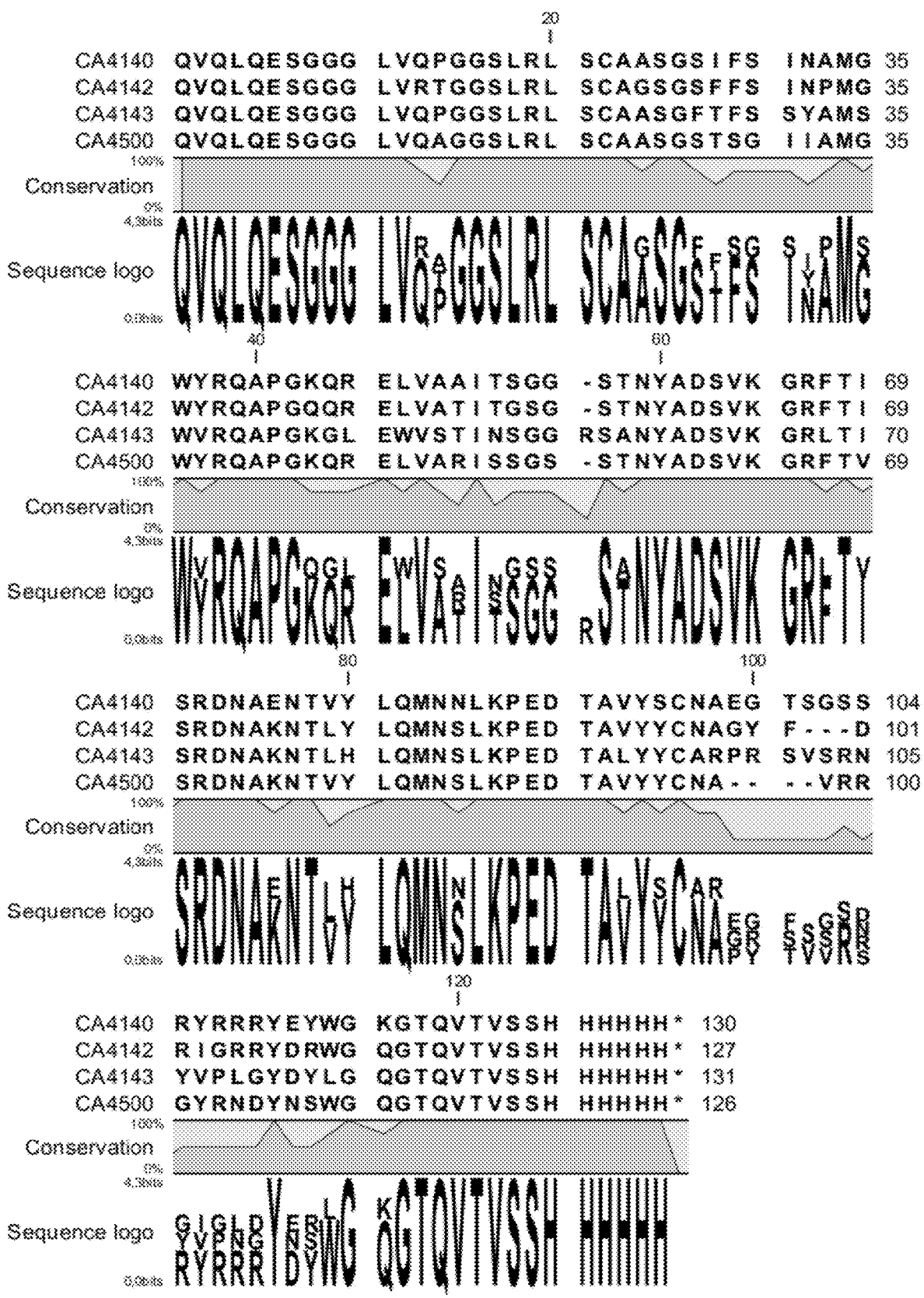
FIG. 1: Protein alignment of the four anti-hCXCR4 Nanobody sequences. The level of conservation between the four different anti-hCXCR4 Nanobodies is graphically depicted as a line plot and a sequence logo (alignment was done using the CLC DNA Workbench software).

The disclosure will be described with respect to particular embodiments and with reference to certain drawings, but the disclosure is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the description and claims, it does not exclude other elements or steps. Where an indefinite or definite article is used when referring to a singular noun, e.g., "a" or "an," "the," this includes a plural of that noun unless something else is specifically stated. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

Unless otherwise defined herein, scientific and technical terms and phrases used in connection with the disclosure shall have the meanings that are commonly understood by those of ordinary skill in the art. Generally, nomenclatures used in connection with, and techniques of molecular and cellular biology, genetics and protein and nucleic acid chemistry and hybridization, described herein, are those well-known and commonly used in the art. The methods and techniques of the disclosure are generally performed according to conventional methods well known in the art and as described in various general and more specific references that are cited and discussed throughout the specification unless otherwise indicated. See, for example, Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002).

Definitions

The term "membrane protein," as used herein, refers to a protein that is attached to or associated with a membrane of a cell or an organelle. Specific non-limiting examples are provided further in the specification.

The term "protein binding domain" or simply "binding domain" refers generally to any non-naturally occurring molecule or part thereof that is able to bind to a protein or peptide using specific intermolecular interactions. A variety of molecules can function as protein binding domains, including, but not limited to, proteinaceous molecules (protein, peptide, protein-like or protein containing), nucleic acid molecules (nucleic acid, nucleic acid-like, nucleic acid containing), and carbohydrate molecules (carbohydrate, carbohydrate-like, carbohydrate containing). A more detailed description can be found further in the specification.

As used herein, the terms "polypeptide," "protein," "peptide" are used interchangeably herein, and refer to a polymeric form of amino acids of any length, which can include coded and non-coded amino acids, chemically or biochemically modified or derivatized amino acids, and polypeptides having modified peptide backbones.

As used herein, the terms "nucleic acid molecule," "polynucleotide," "polynucleic acid," "nucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular.

The term "conformation" or "conformational state" of a protein refers generally to the range of structures that a protein may adopt at any instant in time. One of skill in the art will recognize that determinants of conformation or conformational state include a protein's primary structure as reflected in a protein's amino acid sequence (including modified amino acids) and the environment surrounding the protein. The conformation or conformational state of a protein also relates to structural features such as protein secondary structures (e.g., α-helix, β-sheet, among others), tertiary structure (e.g., the three-dimensional folding of a polypeptide chain), and quaternary structure (e.g., interactions of a polypeptide chain with other protein subunits). Post-translational and other modifications to a polypeptide chain such as ligand binding, phosphorylation, sulfation, glycosylation, or attachments of hydrophobic groups, among others, can influence the conformation of a protein. Furthermore, environmental factors, such as pH, salt concentration, ionic strength, and osmolality of the surrounding solution, and interaction with other proteins and co-factors, among others, can affect protein conformation. The conformational state of a protein may be determined by either functional assay for activity or binding to another molecule or by means of physical methods such as X-ray crystallography, NMR, or spin labeling, among other methods. For a general discussion of protein conformation and conformational states, one is referred to Cantor and Schimmel, Biophysical Chemistry, Part I: The Conformation of Biological. Macromolecules, W.H. Freeman and Company, 1980, and Creighton, Proteins: Structures and Molecular Properties, W.H. Freeman and Company, 1993. A "specific conformational state" is any subset of the range of conformations or conformational states that a protein may adopt.

A "functional conformation" or a "functional conformational state," as used herein, refers to the fact that proteins possess different conformational states having a dynamic range of activity, in particular ranging from no activity to maximal activity. It should be clear that "a functional conformational state" is meant to cover any conformational state of a protein, in particular a membrane protein, having any activity, including no activity; and is not meant to cover the denatured states of proteins. A particular class of functional conformations is defined as "drugable conformation" and generally refers to a unique therapeutically relevant conformational state of a target protein. As an illustration, the active conformation of the β2 adrenergic receptor corresponds to the drugable conformation of this receptor for the treatment of asthma. It will thus be understood that drugability is confined to particular conformations depending on the therapeutic indication.

As used herein, the terms "complementarity determining region" or "CDR" within the context of antibodies refer to variable regions of either H (heavy) or L (light) chains (also abbreviated as VH and VL, respectively) and contains the amino acid sequences capable of specifically binding to antigenic targets. These CDR regions account for the basic specificity of the antibody for a particular antigenic determinant structure. Such regions are also referred to as "hypervariable regions." The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all canonical antibodies each have 3 CDR regions, each non-contiguous with the others (termed L1, L2, L3, H1, H2, H3) for the respective light (L) and heavy (H) chains. Nanobodies, in particular, generally comprise a single amino acid chain that can be considered to comprise 4 "framework sequences or regions" or FRs and 3 "complementarity-determining regions" or CDRs. The nanobodies have 3 CDR regions, each non-contiguous with the others (termed CDR1, CDR2, CDR3). The delineation of the FR and CDR sequences is based on the IMGT unique numbering system for V-domains and V-like domains (Lefranc et al., 2003, Developmental and Comparative Immunology 27:55).

An "epitope," as used herein, refers to an antigenic determinant of a polypeptide. An epitope could comprise 3 amino acids in a spatial conformation, which is unique to the epitope. Generally, an epitope consists of at least 4, 5, 6, 7 such amino acids, and more usually, consists of at least 8, 9, 10 such amino acids. Methods of determining the spatial conformation of amino acids are known in the art, and include, for example, x-ray crystallography and two-dimensional nuclear magnetic resonance.

A "conformational epitope," as used herein, refers to an epitope comprising amino acids in a spatial conformation that is unique to a folded three-dimensional conformation of a polypeptide. Generally, a conformational epitope consists of amino acids that are discontinuous in the linear sequence that come together in the folded structure of the protein. However, a conformational epitope may also consist of a linear sequence of amino acids that adopts a conformation that is unique to a folded three-dimensional conformation of the polypeptide (and not present in a denatured state). In multiprotein complexes, conformational epitopes consist of amino acids that are discontinuous in the linear sequences of one or more polypeptides that come together upon folding of the different folded polypeptides and their association in a unique quaternary structure.

The term "specificity," as used herein, refers to the ability of a binding domain, in particular an immunoglobulin or an immunoglobulin fragment, such as a VHH or nanobody, to bind preferentially to one antigen, versus a different antigen, and does not necessarily imply high affinity.

The term "affinity," as used herein, refers to the degree to which a binding domain, in particular an immunoglobulin, such as an antibody, or an immunoglobulin fragment, such as a VHH or nanobody, binds to an antigen so as to shift the equilibrium of antigen and protein binding domain toward the presence of a complex formed by their binding. Thus, for example, where an antigen and antibody (fragment) are combined in relatively equal concentration, an antibody (fragment) of high affinity will bind to the available antigen so as to shift the equilibrium toward high concentration of the resulting complex. The dissociation constant is commonly used to describe the affinity between the protein binding domain and the antigenic target. Typically, the dissociation constant is lower than $10^{-5}$ M. Preferably, the dissociation constant is lower than $10^{-6}$ M, more preferably, lower than $10^{-7}$ M. Most preferably, the dissociation constant is lower than $10^{-8}$ M.

The terms "specifically bind" and "specific binding," as used herein, generally refers to the ability of a binding domain, in particular an immunoglobulin, such as an antibody, or an immunoglobulin fragment, such as a VHH or nanobody, to preferentially bind to a particular antigen that is present in a homogeneous mixture of different antigens. In certain embodiments, a specific binding interaction will discriminate between desirable and undesirable antigens in a sample, in some embodiments more than about 10- to 100-fold or more (e.g., more than about 1000- or 10,000-fold). Within the context of the spectrum of conformational states of GPCRs, the terms particularly refer to the ability of a binding domain (as defined herein) to preferentially recognize and/or bind to a particular conformational state of a GPCR as compared to another conformational state. For example, an active state-selective protein binding domain will preferentially bind to a GPCR in an active conformational state and will not or to a lesser degree bind to a GPCR in an inactive conformational state, and will thus have a higher affinity for the active conformational state. The terms "specifically bind," "selectively bind," "preferentially bind," and grammatical equivalents thereof, are used interchangeably herein. The terms "conformational specific" or "conformational selective" are also used interchangeably herein.

A "deletion" is defined here as a change in either amino acid or nucleotide sequence in which one or more amino acid or nucleotide residues, respectively, are absent as compared to an amino acid sequence or nucleotide sequence of a parental polypeptide or nucleic acid. Within the context of a protein, a deletion can involve deletion of about 2, about 5, about 10, up to about 20, up to about 30 or up to about 50 or more amino acids. A protein or a fragment thereof may contain more than one deletion. Within the context of a GPCR, a deletion may also be a loop deletion, or an N- and/or C-terminal deletion.

An "insertion" or "addition" is that change in an amino acid or nucleotide sequences, which has resulted in the addition of one or more amino acid or nucleotide residues, respectively, as compared to an amino acid sequence or nucleotide sequence of a parental protein. "Insertion" generally refers to addition to one or more amino acid residues within an amino acid sequence of a polypeptide, while "addition" can be an insertion or refer to amino acid residues added at an N- or C-terminus, or both termini. Within the context of a protein or a fragment thereof, an insertion or addition is usually of about 1, about 3, about 5, about 10, up to about 20, up to about 30 or up to about 50 or more amino acids. A protein or fragment thereof may contain more than one insertion.

A "substitution," as used herein, results from the replacement of one or more amino acids or nucleotides by different amino acids or nucleotides, respectively, as compared to an amino acid sequence or nucleotide sequence of a parental protein or a fragment thereof. It is understood that a protein or a fragment thereof may have conservative amino acid substitutions which have substantially no effect on the protein's activity. By conservative substitutions is intended combinations such as gly, ala; val, ile, leu, met; asp, glu; asn, gln; ser, thr; lys, arg; cys, met; and phe, tyr, trp.

The term "compound" or "test compound" or "candidate compound" or "drug candidate compound," as used herein, describes any molecule, either naturally occurring or synthetic that is tested in an assay, such as a screening assay or drug discovery assay. As such, these compounds comprise organic or inorganic compounds. The compounds include polynucleotides, lipids or hormone analogs that are characterized by low molecular weights. Other biopolymeric organic test compounds include small peptides or peptide-like molecules (peptidomimetics) comprising from about 2 to about 40 amino acids and larger polypeptides comprising from about 40 to about 500 amino acids, such as antibodies, antibody fragments or antibody conjugates. Test compounds can also be protein scaffolds. For high-throughput purposes, test compound libraries may be used, such as combinatorial or randomized libraries that provide a sufficient range of diversity. Examples include, but are not limited to, natural compound libraries, allosteric compound libraries, peptide libraries, antibody fragment libraries, synthetic compound libraries, fragment-based libraries, phage-display libraries, and the like. A more detailed description can be found further in the specification.

As used herein, the term "ligand" means a molecule that specifically binds to a membrane protein, either intracellularly or extracellularly. A ligand may be, without the purpose of being limitative, a protein, a (poly)peptide, a lipid, a small molecule, a protein scaffold, a nucleic acid, an ion, a carbohydrate, an antibody or an antibody fragment, such as a nanobody (all as defined herein). A ligand may be synthetic or naturally occurring. A ligand also includes a "native ligand," which is a ligand that is an endogenous, natural ligand for a native protein. Usually, a membrane protein will adopt a particular conformation upon binding of a ligand. Thus, a ligand is also referred to herein as a "conformation-selective ligand" or "conformation-specific ligand." The term includes agonists, full agonists, partial agonists, inverse agonists, and antagonists, binding at either the orthosteric site or at an allosteric site.

An "orthosteric ligand," as used herein, refers to a ligand (both natural and synthetic), that they binds to the active site of a membrane protein, in particular a receptor protein, such as a GPCR, and are further classified according to their efficacy or in other words to the effect they have on signaling through a specific pathway. As used herein, an "agonist" refers to a ligand that, by binding a membrane protein, increases the membrane protein's signaling activity. Full agonists are capable of maximal protein stimulation; partial agonists are unable to elicit full activity even at saturating concentrations. Partial agonists can also function as "blockers" by preventing the binding of more robust agonists. An "antagonist" refers to a ligand that binds a membrane protein without stimulating any activity. An "antagonist" is also known as a "blocker" because of its ability to prevent binding of other ligands and, therefore, block agonist-induced activity. Further, an "inverse agonist" refers to an antagonist that, in addition to blocking agonist effects, reduces a membrane proteins' basal or constitutive activity below that of the unliganded protein.

Ligands, as used herein, may also be "biased ligands" with the ability to selectively stimulate a subset of a membrane protein's signaling activities, for example, in the case of GPCRs the selective activation of G-protein or β-arrestin function. Such ligands are known as "biased ligands," "biased agonists" or "functionally selective agonists." More particularly, ligand bias can be an imperfect bias characterized by a ligand stimulation of multiple membrane protein activities with different relative efficacies for different signals (non-absolute selectivity) or can be a perfect bias characterized by a ligand stimulation of one membrane protein activity without any stimulation of another known membrane protein activity.

Another kind of ligands is known as allosteric regulators. "Allosteric regulators" or otherwise "allosteric modulators," "allosteric ligands" or "effector molecules," as used herein, refer to ligands that bind at an allosteric site (that is, a regulatory site physically distinct from the protein's active site) of a membrane protein, in particular a receptor protein such as a GPCR. In contrast to orthosteric ligands, allosteric modulators are non-competitive because they bind membrane proteins at a different site and modify their function even if the endogenous ligand also is binding. Allosteric regulators that enhance the protein's activity are referred to herein as "allosteric activators" or "positive allosteric modulators," whereas those that decrease the protein's activity are referred to herein as "allosteric inhibitors" or otherwise "negative allosteric modulators."

As used herein, the terms "determining," "measuring," "assessing," "monitoring" and "assaying" are used interchangeably and include both quantitative and qualitative determinations.

The term endogenous," as used herein, refers to substances (e.g., genes) originating from within an organism, tissue, or cell. Analogously, "exogenous," as used herein, is any material that comes from outside an organism, tissue, or cell, but that is present (and typically can become active) in that organism, tissue, or cell.

The term "inducible promoter," as used herein, refers to a promoter that can be switched "on" or "off" (thereby regulating gene transcription) in response to external stimuli such as, but not limited to, temperature, pH, certain nutrients, specific cellular signals, etcetera. It is used to distinguish between a "constitutive promoter," by which a promoter is meant that is continuously switched "on," i.e., from which gene transcription is constitutively active.

The term "subcellular targeting sequence," as used herein, generally refers to a molecule that directs localization of proteins to different cell compartments. Examples include an "ER localization signal" or a "Golgi localization signal," which is a molecule, typically a peptide that directs localization of the polypeptide or protein to which it is conjugated to the ER or Golgi apparatus, respectively. Localization, thus, also implies retention in the ER or Golgi apparatus, respectively. Typically, these localization (or retention) sequences are peptide sequences derived from (pre)proteins that are situated in the ER or Golgi when functionally active as a mature protein and examples are provided further herein. In particular, the C-terminal addition of the tetrapeptide H/KDEL to a soluble protein that is translocated in the ER can be used to retain this protein in the ER. Subcellular targeting sequences also include secretion signals of which examples are also provided further herein.

The term "vector," as used herein, is intended to refer to a nucleic acid molecule capable of transporting another nucleic acid molecule to which it has been linked. One type of vector is a "plasmid vector," which refers to a circular double stranded DNA loop into which additional DNA segments may be ligated. Other vectors include, without the purpose of being limitative, cosmids and yeast artificial chromosomes (YAC). Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain preferred vectors are capable of directing the expression of certain genes of interest. Such vectors are referred to herein as "recombinant expression vectors" (or simply, "expression vectors"). Suitable vectors have regulatory sequences, such as promoters, enhancers, terminator sequences, and the like as desired.

The term "regulatory sequence," as used herein, refers to polynucleotide sequences, which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRMA; sequences that enhance translation efficiency (e.g., ribosome binding sites); sequences that enhance protein stability; and when desired, sequences that enhance protein secretion. The nature of such control sequences differs depending upon the host organism. The term "control sequences" is intended to include, at a minimum, all components whose presence is essential for expression, and can also include additional components whose presence is advantageous, for example, leader sequences and fusion partner sequences.

The term "operably linked," as used herein, refers to a linkage in which the regulatory sequence is contiguous with the gene of interest to control the gene of interest, as well as regulatory sequences that act in trans or at a distance to control the gene of interest.

The term "host cell" and equivalent terms like "recombinant host cell," "expression host cell," "expression host system," "expression system," as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell," as used herein. A recombinant host cell may be an isolated cell or cell line grown in culture or may be a cell which resides in a living tissue or organism. Particular examples are provided further herein.

Detailed Description

The disclosure provides engineered cells or cellular systems (cell cultures, organisms) that can express proteins, particularly membrane proteins, at higher levels either at the cellular surface or in other cell compartments. In particular, the proteins that are expressed by these cells or cellular systems are maintained or stabilized in a particular functional conformation. Further, methods are provided that use such cells or cellular systems to produce these proteins. It will be appreciated that while the disclosure has been exemplified with GPCRs, it is equally applicable to any membrane protein, especially a membrane protein that is poorly expressed and has a low stability in a recombinant host cell.

Accordingly, a first aspect of the disclosure relates to a host cell comprising a first exogenous nucleic acid sequence encoding a membrane protein and a second exogenous nucleic acid encoding a binding domain directed against the membrane protein, each under the control of a promoter.

The "host cell," according to the disclosure, can be of any prokaryotic or eukaryotic organism. According to a preferred embodiment, the host cell is a eukaryotic cell and can be of any eukaryotic organism, but in particular embodiments yeast, plant, mammalian and insect cells are envisaged. The nature of the cells used will typically depend on the ease and cost of producing the native protein(s), the desired glycosylation properties, the origin of the target protein, the intended application, or any combination thereof. Mammalian cells may, for instance, be used for achieving complex glycosylation, but it may not be cost-effective to produce proteins in mammalian cell systems. Plant and insect cells, as well as yeast typically achieve high production levels and are more cost-effective, but additional modifications may be needed to mimic the complex glycosylation patterns of mammalian proteins or to avoid excessive glycosylation heterogeneity which might hamper crystal formation or structural determination. Yeast cells are currently preferred for expression of proteins because they can be economically cultured, give high yields of protein, and when appropriately modified are capable of producing proteins having suitable glycosylation patterns. Further, yeast offers established genetics allowing for rapid transformations, tested protein localization strategies, and facile gene knock-out techniques. Eukaryotic cell or cell lines for protein production are well known in the art, including cell lines with modified glycosylation pathways, and non-limiting examples will be provided hereafter.

Animal or mammalian host cells suitable for harboring, expressing, and producing proteins for subsequent isolation and/or purification may be from human or non-human origin, and include Chinese hamster ovary cells (CHO), such as CHO-K1 (ATCC CCL-61), DG44 (Chasin et al., 1986, Som. Cell Molec. Genet., 12:555-556; and Kolkekar et al., 1997, Biochemistry, 36:10901-10909), CHO-K1 Tet-On cell line (Clontech), CHO designated ECACC 85050302 (CAMR, Salisbury, Wiltshire, UK), CHO clone 13 (GEIMG, Genova, IT), CHO clone B (GEIMG, Genova, IT), CHO-K1/SF designated ECACC 93061607 (CAMR, Salisbury, Wiltshire, UK), RR-CHOK1 designated ECACC 92052129 (CAMR, Salisbury, Wiltshire, UK), dihydrofolate reductase negative CHO cells (CHO/−DHFR, Urlaub and Chasin, 1980, Proc. Natl. Acad. Sci. USA, 77:4216), and dp12.CHO cells (U.S. Pat. No. 5,721,121); monkey kidney CV1 cells transformed by SV40 (COS cells, COS-7, ATCC CRL-1651); human embryonic kidney cells (e.g., 293 cells, or 293T cells, or 293 cells subcloned for growth in suspension culture, Graham et al., 1977, J. Gen. Virol., 36:59, or GnTI KO HEK293S cells, Reeves et al., 2002, PNAS, 99: 13419); baby hamster kidney cells (BHK, ATCC CCL-10); monkey kidney cells (CV1, ATCC CCL-70); African green monkey kidney cells (VERO-76, ATCC CRL-1587; VERO, ATCC CCL-81); mouse sertoli cells (TM4, Mather, 1980, Biol. Reprod., 23:243-251); human cervical carcinoma cells (HELA, ATCC CCL-2); canine kidney cells (MDCK, ATCC CCL-34); human lung cells (W138, ATCC CCL-75); human hepatoma cells (HEP-G2, HB 8065); mouse mammary tumor cells (MMT 060562, ATCC CCL-51); buffalo rat liver cells (BRL 3A, ATCC CRL-1442); TRI cells (Mather, 1982, Annals NYAcad. Sci., 383:44-68); MCR 5 cells; FS4 cells. According to a particular embodiment, the cells are mammalian cells selected from Hek293 cells or COS cells.

Exemplary non-mammalian cell lines include, but are not limited to, Sf9 cells, baculovirus-insect cell systems (e.g., review Jarvis, Virology Volume 310, Issue 1, May 25, 2003, Pages 1-7), plant cells such as tobacco cells, tomato cells, maize cells, algae cells, or yeasts such as *Saccharomyces* species, *Schizosaccharomyces* species, *Hansenula* species, *Yarrowia* species or *Pichia* species. According to particular embodiments, the eukaryotic cells are yeast cells from a *Saccharomyces* species (e.g., *Saccharomyces cerevisiae*), *Schizosaccharomyces* sp. (for example, *Schizosaccharomyces pombe*), a *Hansenula* species (e.g., *Hansenula polymorpha*), a *Yarrowia* species (e.g., *Yarrowia lipolytica*), a *Kluyveromyces* species (e.g., *Kluyveromyces lactis*), a *Pichia* species (e.g., *Pichia pastoris*), or a *Komagalaella* species (e.g., *Komagataella pastoris*). According to a specific embodiment, the eukaryotic cells are *Pichia* cells, and in a most particular embodiment *Pichia pastoris* cells.

By "membrane protein" is understood a protein that is attached to or associated with a membrane of a cell or an organelle. They are often subdivided into several categories including integral membrane proteins, peripheral membrane proteins and lipid-anchored proteins. Preferably, the membrane protein is an integral membrane protein that is permanently bound to the lipid bilayer and which requires a detergent or another apolar solvent to be removed. Integral membrane proteins include transmembrane proteins that are permanently attached to the lipid membrane and span across the membrane one or several times. Examples of suitable membrane proteins include receptors such as GPCRs and growth factor receptors; transmembrane ion channels such as ligand-gated and voltage gated ion channels; transmembrane transporters such as neurotransmitter transporters; enzymes; carrier proteins; ion pumps; viral membrane proteins and supramolecular complexes thereof, amongst others.

Depending on their intended use, membrane proteins as referred to herein can be of any species, such as fungus (including yeast), nematode, virus, insect, plant, bird (e.g., chicken, turkey), reptile, or mammal (e.g., a mouse, rat, rabbit, hamster, gerbil, dog, cat, goat, pig, cow, horse, whale, monkey, or human).

In a specific embodiment, the membrane protein is a G-protein coupled receptor or GPCR. GPCRs can be grouped on the basis of sequence homology into several distinct families. Although all GPCRs have a similar architecture of seven membrane-spanning α-helices, the different families within this receptor class show no sequence homology to one another, thus suggesting that the similarity of their transmembrane domain structure might define common functional requirements. GPCR structure and classification is generally well known in the art and further discussions of GPCRs may be found in Probst et al., 1992, DNA Cell Biol. 1:1; Marchese et al., 1994, Genomics 23:609; Rosenbaum et al., 2009, Nature 459:356; and the following books: Jurgen Wess (Ed) Structure-Function Analysis of G Protein-Coupled Receptors published by Wiley-Liss (1st edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994). A comprehensive view of the GPCR repertoire was possible when the first draft of the human genome became available. Fredriksson and colleagues divided 802 human GPCRs into families on the basis of phylogenetic criteria. This showed that most of the human GPCRs can be found in five main families, termed Glutamate, Rhodopsin, Adhesion, Frizzled/Taste2 and Secretin (Fredriksson et al., 2003, Molecular Pharmacology 63:1256).

GPCRs include, without limitation, serotonin and olfactory receptors, glycoprotein hormone receptors, chemokine receptors, adenosine receptors, biogenic amine receptors, melanocortin receptors, neuropeptide receptors, chemotactic receptors, somatostatin receptors, opioid receptors, melatonin receptors, calcitonin receptors, PTH/PTHrP receptors, glucagon receptors, secretin receptors, latrotoxin receptors, metabotropic glutamate receptors, calcium receptors, GABA-B receptors, pheromone receptors, histamine receptors, protease-activated receptors, rhodopsins and other G-protein coupled seven transmembrane segment receptors. GPCRs also include these GPCR receptors associated with each other as homomeric or heteromeric dimers or as higher-order oligomers. The amino acid sequences (and the nucleotide sequences of the cDNAs which encode them) of GPCRs are readily available, for example, by reference to GenBank (on the World Wide Web at ncbi.nlm.nih.gov/entrez). Specific examples of GPCRs envisaged for increased production using the tools and methods provided herein include, but are not limited to, CXCR4, GPR3, rhodopsin, vasopressin receptor, β1 adrenergic receptor, β2 adrenergic receptor, β3 adrenergic receptor, α1 adrenergic receptors and the α2 adrenergic receptor, M1 muscarinic receptor, M2 muscarinic receptor, M3 muscarinic receptor, M4 muscarinic receptor, M5 muscarinic receptor, angiotensin II receptors.

Notably, fragments or portions, or mutants, variants, or analogues of any of the aforementioned proteins and polypeptides are also included among the suitable proteins, polypeptides and peptides that can be produced by the cells and methods presented herein. In particular, a membrane protein, as used herein, may be any naturally occurring or non-naturally occurring (i.e., altered by man) membrane protein. Within this context, the term "naturally-occurring" means a membrane protein that is naturally produced (for example, and without limitation, by a mammal, more specifically by a human, or by a virus, or by a plant, or by an insect, amongst others). Such membrane proteins are found in nature. Analogously, the term "non-naturally occurring" means a membrane protein that is not naturally produced. Wild-type membrane proteins that have been made constitutively active through mutation, and variants of naturally occurring membrane proteins are examples of non-naturally occurring membrane proteins. Non-naturally occurring membrane proteins may have an amino acid sequence that is at least 80% identical to, at least 90% identical to, at least 95% identical to or at least 99% identical to, a naturally-occurring membrane protein. Taking the CXCR4 receptor as a particular non-limiting example of a GPCR within the scope of the disclosure, it should be clear from the above that in addition to the human CXCR4 receptor (e.g., the sequence described by Genbank accession number EAX11616, Gene ID 7852), the mouse CXCR4 receptor (e.g., as described by Genbank accession number NP_034041, Gene ID 12767) or other mammalian CXCR4 receptor may also be employed. In addition, the term is intended to encompass wild-type polymorphic variants and certain other active variants from a particular species. For example, a "human CXCR4 receptor" has an amino acid sequence that is at least 95% identical to (e.g., at least 95% or at least 98% identical to) the naturally occurring "human CXCR4" of Genbank accession number EAX11616, Gene ID 7852. Further, it will be appreciated that the disclosure also envisages membrane proteins, in particular GPCRs, with a loop deletion, or an N- and/or C-terminal deletion, or a substitution, or an insertion or addition in relation to its amino acid or nucleotide sequence, or any combination thereof (as defined hereinbefore), or a membrane protein in complex with another chemical entity such as one or more interacting proteins or an agonist/antagonist/inverse agonist.

Thus, according to specific embodiments, the tools and methods for membrane protein expression provided herein can be further combined with known improvements for membrane protein expression that typically involve production of variants. Examples thereof include, but are not limited to, the use of a signal sequence specific to the species of eukaryotic cell used rather than the membrane protein-specific signal sequence, the use of a truncated membrane protein (e.g., C-truncated) versus the use of an intact protein, the use of a membrane protein with a sequence insertion (e.g., a T4 lysozyme coding sequence in the $3^{rd}$ intracellular loop of a GPCR), and so on. Of course, these different variations can further be combined with each other.

According to still other specific embodiments, more than one, i.e., two or more different proteins may be produced simultaneously. Preferably, at least one of the proteins is a membrane protein. The proteins may all be membrane-bound, all be secreted proteins or a mixture thereof. When more than one protein is produced, care will be taken that they can be recovered easily either separately or together. In a specific embodiment, even higher production is achieved by expressing multiple copies of the protein to be expressed, e.g., as a polyprotein.

Preferably, the produced (membrane) proteins are functional, for instance, the produced receptors remain capable of ligand binding and/or signal transduction.

The host cell, according to the disclosure, is engineered so to express a membrane protein as well as a binding domain directed against the membrane protein. By "binding domain" is meant any non-naturally occurring molecule or part thereof (as defined hereinbefore) that is directed against a target membrane protein. In a preferred embodiment, the binding domains, as described herein, are protein scaffolds. Protein scaffolds refer generally to folding units that form structures, particularly protein or peptide structures, that comprise frameworks for the binding of another molecule, for instance, a protein (see, e.g., review of Skerra, J. 2000, Molecular Recognition, 13:167). Accordingly, a binding domain can be derived from a naturally occurring molecule, e.g., from components of the innate or adaptive immune system, or it can be entirely artificially designed. A binding domain can be immunoglobulin-based or it can be based on domains present in proteins including, but not limited to, microbial proteins, protease inhibitors, toxins, fibronectin, lipocalins, single chain antiparallel coiled coil proteins or repeat motif proteins. Examples of binding domains, which are known in the art include, but are not limited to: antibodies, heavy chain antibodies (hcAb), single domain antibodies (sdAb), minibodies, the variable domain derived from camelid heavy chain antibodies (VHH or nanobodies), the variable domain of the new antigen receptors derived from shark antibodies (VNAR), alphabodies, protein A, protein G, designed ankyrin-repeat domains (DARPins), fibronectin type III repeats, anticalins, knottins, engineered CH2 domains (nanoantibodies), peptides and proteins, lipopeptides (e.g., pepducins), DNA, and RNA (see, e.g., Gebauer & Skerra, 2009, Curr Opin Chem Biol. 13:245; Skerra, 2000, Molecular Recognition, 13:167; Starovasnik et al., 1997, Proc Natl Acad Sci USA. 94:10080; Binz et al., 2004, Nature Biotech., 22: 575; Koide et al., 1998, J. Mol. Biol., 284:1141; Dimitrov, 2009, MAbs. 1:26; Nygren et al., 2008, FEBS J. 275:2668; WO2010066740). Frequently, when generating a particular type of binding domain using selection methods, combinatorial libraries comprising a consensus or framework sequence containing randomized potential interaction residues are used to screen for binding to a molecule of interest, such as a protein.

The binding domain, according to the disclosure, may generally be directed against any desired membrane protein, as described hereinbefore, and may in particular be directed against any conformational epitope of any membrane protein, preferably a functional conformational state of any membrane protein (active, inactive, etc.). More particularly, the conformational epitope can be part of an intracellular or extracellular region, or an intramembraneous region, or a domain or loop structure of any desired membrane protein. According to particular embodiments, the binding domains may be directed against any suitable extracellular region, domain, loop or other extracellular conformational epitope of a membrane protein, but is preferably directed against one of the extracellular parts of the transmembrane domains or more preferably against one of the extracellular loops that link the transmembrane domains. Alternatively, the protein binding domains may be directed against any suitable intracellular region, domain, loop or other intracellular conformational epitope of a membrane protein, but is preferably directed against one of the intracellular parts of the transmembrane domains or more preferably against one of the intracellular loops that link the transmembrane domains. A binding domain that specifically binds to a "three-dimensional" epitope or "conformational" epitope specifically binds to a tertiary (i.e., three-dimensional) structure of a folded protein, and binds at much reduced (i.e., by a factor of at least 2, 5, 10, 50 or 100) affinity to the linear (i.e., unfolded, denatured) form of the protein.

According to other preferred embodiments, the expression of the proteins in the host cell, as described herein, is preferably regulated by appropriate promoters. The choice of a promoter will typically depend on the nature of the host cell. The choice further depends on the desired temporal expression of a particular protein, as described herein. The proteins may be expressed constitutively or in an inducible way. Accordingly, the promoter may be a constitutive or inducible promoter. The conditions for inducing a promoter may be chosen from the following group of inducing conditions: metabolic, or stress, or pH, or temperature, or drug inducing conditions, or other. Promoters may be derived directly from naturally occurring genes, or may be synthesized to combine regulatory sequences from different promoter regions. Preferably, the promoter is an exogenous promoter that will typically be strong enough to ensure overexpression of the protein(s).

In a preferred embodiment, the promoter is an inducible promoter. Examples of inducible promoters useful for the practice of the disclosure, in particular for yeast cells, include, without limitation, the promoter of a gene selected from the group comprising alcohol oxidase I (AOX1) (Tschopp et al., 1987, Nucleic Acids Res. 15:3859), alcohol oxidase II (AOXII) (Ohi et al., 1994, Mol. Gen. Genet. 243:489), formaldehyde dehydrogenase (FLD) (U.S. Pat. No. 6,730,499; Shen et al., 1998, Gene 216:93), galactokinase (GAL1) (Flick and Johnston 1990, Mol. Cell Biol. 10:4757), methanol oxidase (MOX) (GOdeke et al., 1994, Gene 139:35), formate dehydrogenase (FMD) (Eggeling and Sahm 1978, Eur. J. Appl. Microbiol. Biotechnol. 5:197), mitochondrial alternative oxidase (AOD1) (Kern et al., 2007, Microbiology. 153:1250), peroxisomal acyl coenzyme A oxidase (POX1) (Koller et al., 1999, Yeast 15, 1035). Other examples typically for mammalian cells include the doxycycline-inducible system with reverse tetracycline-controlled transactivator (rtTA) and tetracycline-responsive element promoter (TRE) (Qin et al., 2010, Plos One 5:e10611).

Alternatively, constitutive promoters may be used and include, for example, the glyceraldehyde-3-phosphate dehydrogenase promoter (GAP) (Zhang et al., 2009, Mol. Biol. Rep 0.36: 1611) for expression in yeast; the simian virus 40 early promoter (SV40), the cytomegalovirus immediate-early promoter (CMV), the human Ubiquitin C promoter (UBC), the human elongation factor 1a promoter (EF1A), the mouse phosphoglycerate kinase 1 promoter (PGK), the chicken b-Actin promoter coupled with CMV early enhancer (CAGG) for expression in mammalian cells (Qin et al., 2010, Plos One 5:e10611).

According to a preferred embodiment, the disclosure relates to a host cell engineered, as described hereinbefore, wherein the membrane protein and the binding domain are co-expressed. By "co-expressed" is meant temporally expressed at the same time or simultaneously expressed, which can be regulated by choosing the appropriate promoter(s) (as described hereinbefore).

Further, it is preferred that upon expression in the host cell, the membrane protein and the binding domain are co-localized in a particular cellular compartment, such as in the ER, in the Golgi apparatus, at the cellular surface (meaning the membrane protein attached to the cell membrane and the binding domain co-localized at the extracellular or intracellular side of the cell membrane). By "co-localized" is meant spatially expressed at the same cellular location. This can be done by operably linking the membrane protein and/or the binding domain to an appropriate subcellular targeting sequence, as defined herein, such as an ER or Golgi localization signal, or a secretion signal, or combinations thereof.

Depending on the application (see further herein), the membrane protein and binding domain are preferably co-expressed and translocated to the cellular surface or to the extracellular space. This will typically be achieved by making use of secretion signals, so that the co-expressed proteins are transported through the secretory pathway: from the ER to the cis-, medial- and trans-Golgi compartments, finally resulting in secretion into the extracellular medium, or otherwise integration in the cellular membrane, which is typically the case for membrane proteins. Preferably, both the membrane protein and the binding domain are operably linked to a secretion signal. Even more preferably, both the membrane protein and the binding domain are operably linked to the same secretion signal. The nature of the secretion signal will typically not depend on the protein to be secreted, but on the type of eukaryotic cells used. As long as the secretion signal is functional in the cell type in which it is used (i.e., it results in secretion to the extracellular environment (or to the cellular membrane) of the protein or peptide to which it is fused), this feature is not critical to the disclosure. Thus, secretion signals from other organisms may be used, as long as these signals lead to secretion in the eukaryotic cells used. Secretion signals are well known in the art and may be derived from—typically the N-terminus of—proteins that are secreted, or may be made synthetically (e.g., Tan et al., Protein engineering 2002, 15:337). Alternatively, they can be derived from genomic sequences using computational methods (Klee et al., BMC Bioinformatics 2005, 6:256). Also, viral or bacterial or even hybrid secretion signals can be used. Further examples of signal peptides that can be used are described in WO2002/048187 (eukaryotic cells), Schaaf et al. (BMC Biotechnol. 2005; 5: 30) (moss cells), EP549062. Specific secretion signals used in yeast include, e.g., α-factor secretory peptide, the PH05 secretory peptide, and the BARI secretion signal. In particular, secretion signals derived from the *Pichia* genome sequence have been described in WO2010/135678.

Alternatively, the membrane protein and binding domain may also be co-expressed and retained in the ER or Golgi compartment. ER and Golgi localization signals are well known in the art and may be derived from proteins that are normally localized in the ER or Golgi for their function. Again, localization sequences from one organism may function in other organisms. For example, the membrane spanning region of α-2,6-sialyltransferase from rats, an enzyme known to localize in the rat trans Golgi, was shown to also localize a reporter gene (invertase) in the yeast Golgi (Schwientek, et al., 1995, J. Biol. Chem. 270:5483). Schwientek and co-workers have also shown that fusing 28 amino acids of a yeast mannosyltransferase (Mnt1), a region containing an N-terminal cytoplasmic tail, a transmembrane region and eight amino acids of the stem region, to the catalytic domain of human GalT are sufficient for Golgi localization of an active GalT (Schwientek et al., 1995 J. Biol. Chem. 270 (10): 5483-5489). Other well-documented motifs are the KDEL and HDEL motif for retention in the ER as well as other sequences listed in Table 5 of WO02/000879 such as the leader sequences from MnsI for ER localization, and leader sequences from Och1 and Mnt1 (Golgi-cis localization), from Mnn2 (Golgi medial localization), from Mnn1 (Golgi trans localization), from alpha-2, 6-sialyltransferase (trans-Golgi network) and from beta-1, 4-galactosyltransferase I (Golgi localization).

Alternatively, the membrane protein and binding domain may also be co-expressed and deposited in inclusion bodies in the cell, or in membrane-bound organelles or in structures with similar functions. When cells are part of an organism that is used for production (e.g., a plant instead of a plant cell culture), the co-expressed proteins may be produced in or transported to specific organs or tissues of the organism from which it can be recovered (e.g., glands or trichomes). It should be noted that, particularly in cases where the protein is not secreted, it is possible that the protein is deposited in an inactive form. Thus, additional refolding or re-activating steps may be needed in order to obtain a physiologically relevant form of the protein.

According to a preferred embodiment of the disclosure, it is particularly envisaged that the binding domain which is co-expressed with the membrane protein, as described hereinbefore, is derived from an innate or adaptive immune system. Preferably, the binding domain is derived from an immunoglobulin. Preferably, the protein binding domain, according to the disclosure, is an antibody or a derivative thereof. The term "antibody" (Ab) refers generally to a polypeptide encoded by an immunoglobulin gene, or functional fragments thereof that specifically binds and recognizes an antigen, and is known to the person skilled in the art. A conventional immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains, respectively. The term "antibody" is meant to include whole antibodies, including single-chain whole antibodies, and antigen-binding fragments. In some embodiments, antigen-binding fragments may be antigen-binding antibody fragments that include, but are not limited to, Fab, Fab' and F(ab')2, Fd, single-chain Fvs (scFv), single-chain antibodies, disulfide-linked Fvs (dsFv) and fragments comprising or consisting of either a VL or VH domain, and any combination of those or any other functional portion of an immunoglobulin peptide capable of binding to the target antigen. The term "antibodies" is also meant to include heavy chain antibodies, or functional fragments thereof, such as single domain antibodies, more specifically, VHHs or nanobodies, as defined further herein.

Preferably, the binding domain is an immunoglobulin single variable domain. More preferably, the binding domain comprises an amino acid sequence comprising 4 framework regions and 3 complementarity-determining regions, preferably in a sequence FR1-CDR1-FR2-CDR2-FR3-CDR3-FR4, or any suitable fragment thereof (which will then usually contain at least some of the amino acid residues that form at least one of the complementarity-determining regions). Binding domains comprising 4 FRs and 3 CDRs are known to the person skilled in the art and have been described, as a non-limiting example, in Wesolowski et al., 2009, Med. Microbiol. Immunol. 198:157.

Preferably, the binding domain, according to the disclosure, is derived from a camelid antibody. More preferably, the binding domain, according to the disclosure, comprises an amino acid sequence of a nanobody, or any suitable fragment thereof. More specifically, the protein binding domain is a nanobody or any suitable fragment thereof. A "nanobody" (Nb), as used herein, refers to the smallest antigen binding fragment or single variable domain ("VHH") derived from a naturally occurring heavy chain antibody and is known to the person skilled in the art. They are derived from heavy chain only antibodies, seen in camelids (Hamers-Casterman et al., 1993, Nature 363:446; Desmyter et al., 1996, Nat. Struct. Biol. 3:803). In the family of "camelids" immunoglobulins devoid of light polypeptide chains are found. "Camelids" comprise old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a nanobody or a VHH. NANOBODY®, NANOBODIES® and NANOCLONE® are trademarks of Ablynx NV (Belgium). The small size and unique biophysical properties of Nbs excel conventional antibody fragments for the recognition of uncommon or hidden epitopes and for binding into cavities or active sites of protein targets. Further, Nbs can be designed as bispecific and bivalent antibodies or attached to reporter molecules (Conrath et al., 2001, Antimicrob. Agents Chemother. 45: 2807). Nbs are stable and rigid single domain proteins that can easily be manufactured and survive the gastro-intestinal system. Therefore, Nbs can be used in many applications including drug discovery and therapy (Saerens et al., 2008, Curr. Opin. Pharmacol. 8:600) but also as a versatile and valuable tool for purification, functional study and crystallization of proteins (Conrath et al., 2009, Protein Sci. 18:619). In that regard, a particular class of nanobodies that act as crystallization chaperones binding conformational epitopes of native targets are called Xaperones and are also envisaged here. Xaperones are unique tools in structural biology. XAPERONE™ is a trademark of VIB and VUB (Belgium). Major advantages for the use of camelid antibody fragments as crystallization aid are that Xaperones (1) bind cryptic epitopes and lock proteins in unique native conformations, (2) increase the stability of soluble proteins and solubilized membrane proteins, (3) reduce the conformational complexity of soluble proteins and solubilized membrane proteins, (4) increase the polar surface enabling the growth of diffracting crystals, (5) sequester aggregative or polymerizing surfaces, (6) allow to affinity-trap active protein.

The nanobodies, according to the disclosure, generally comprise a single amino acid chain that can be considered to comprise 4 "framework sequences" or FR's and 3 "complementarity-determining regions" or CDR's (as defined hereinbefore). Non-limiting examples of nanobodies of the disclosure are described in more detail further herein. It should be clear that framework regions of nanobodies may also contribute to the binding of their antigens (Desmyter et al., 2002, J. Biol. Chem. 277:23645; Korotkov et al., 2009, Structure 17:255).

It should be noted that the term nanobody, as used herein, in its broadest sense is not limited to a specific biological source or to a specific method of preparation. For example, the nanobodies of the disclosure can generally be obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a mammalian species, such as from a human being, or by expression of a nucleic acid encoding such a camelized VH domain; (5) by "camelization" of a "domain antibody" or "Dab," as described in the art, or by expression of a nucleic acid encoding such a camelized VH domain; (6) by using synthetic or semi-synthetic techniques for preparing proteins, polypeptides or other amino acid sequences known per se; (7) by preparing a nucleic acid encoding a nanobody using techniques for nucleic acid synthesis known per se, followed by expression of the nucleic acid thus obtained; and/or (8) by any combination of one or more of the foregoing.

According to a preferred embodiment, the nanobodies or VHHs are directed against a functional conformational state of a membrane protein, as described hereinbefore. Although naive or synthetic libraries of nanobodies (for examples of such libraries, see WO9937681, WO0043507, WO0190190, WO03025020 and WO03035694) may contain conformational binders against a membrane protein in a functional conformational state, a preferred embodiment of this disclosure includes the immunization of a Camelidae with a membrane protein in a functional conformational state, optionally bound to a ligand, to expose the immune system of the animal with the conformational epitopes that are unique to the membrane protein in that particular conformation (for example, agonist-bound GPCR so as to raise antibodies directed against a GPCR in its active conformational state; or antagonist-bound GPCR so as to raise antibodies directed against a GPCR in its inactive conformational state). Thus, as further described herein, such VHH sequences can preferably be generated or obtained by suitably immunizing a species of Camelid with a target membrane protein, preferably a membrane protein in a functional conformational state (i.e., so as to raise an immune response and/or heavy chain antibodies directed against the membrane protein), by obtaining a suitable biological sample from the Camelid (such as a blood sample, or any sample of B-cells), and by generating VHH sequences directed against the membrane protein, starting from the sample. Such techniques will be clear to the skilled person. Yet another technique for obtaining the desired VHH sequences involves suitably immunizing a transgenic mammal that is capable of expressing heavy chain antibodies (i.e., so as to raise an immune response and/or heavy chain antibodies directed against a membrane protein in a functional conformational state), obtaining a suitable biological sample from the transgenic mammal (such as a blood sample, or any sample of B-cells), and then generating VHH sequences directed against the membrane protein starting from the sample, using any suitable technique known per se. For example, for this purpose, the heavy chain antibody-expressing mice and the further methods and techniques described in WO02085945 and in WO04049794 can be used.

Non-limiting examples of the nanobodies, according to the disclosure, include, but are not limited to, nanobodies as defined by SEQ ID NOS:1-6 (see Table 1). The delineation of the CDR sequences is based on the IMGT unique numbering system for V-domains and V-like domains (Lefranc et al., 2003, Developmental and Comparative Immunology 27:55). In a specific embodiment, the above nanobodies can comprise at least one of the complementarity-determining regions (CDRs) with an amino acid sequence selected from SEQ ID NOS:7-24 (see Table 2). More specifically, the above nanobodies can be selected from the group comprising SEQ ID NOS: 1-6, or a functional fragment thereof. A "functional fragment" or a "suitable fragment," as used herein, may, for example, comprise one of the CDR loops. Preferably, the functional fragment comprises CDR3. More specifically, the nanobodies consist of any of SEQ ID NOS:1-6 and the functional fragment of said nanobodies consist of any of SEQ ID NOS:7-24. Further, nucleic acid sequences encoding any of the above nanobodies or functional fragments are also envisaged in the disclosure.

It is also within the scope of the disclosure to use natural or synthetic analogs, mutants, variants, alleles, homologs and orthologs (herein collectively referred to as "analogs") of the binding domains, according to the disclosure, preferably to the nanobodies, and in particular analogs of the nanobodies of SEQ ID NOS:1-6 (see Table 1). Thus, according to one embodiment of the disclosure, the term "nanobody of the disclosure" in its broadest sense also covers such analogs. Generally, in such analogs, one or more amino acid residues may have been replaced, deleted and/or added, compared to the nanobodies of the disclosure, as defined herein. Such substitutions, insertions, deletions or additions may be made in one or more of the framework regions and/or in one or more of the CDR's. Analogs, as used herein, are sequences wherein each or any framework region and each or any complementarity-determining region shows at least 80% identity, preferably at least 85% identity, more preferably 90% identity, even more preferably 95% identity with the corresponding region in the reference sequence (i.e., FR1_analog versus FR1_reference, CDR1_analog versus CDR1_reference, FR2_analog versus FR2_reference, CDR2_analog versus CDR2_reference, FR3_analog versus FR3_reference, CDR3_analog versus CDR3_reference, FR4_analog versus FR4_reference), as measured in a BLASTp alignment (Altschul et al., 1997, Nucleic Acids Res. 25:3389; FR and CDR definitions according to IMGT unique numbering system for V-domains and V-like domains (Lefranc et al., 2003, Developmental and Comparative Immunology 27:55)). Non-limiting examples include analogs of the CDR's of the nanobodies of SEQ ID NOS:1-6, the CDR's corresponding with SEQ ID NOS:7-24 (see Table 2).

By means of non-limiting examples, a substitution may, for example, be a conservative substitution, as defined herein, and/or an amino acid residue may be replaced by another amino acid residue that naturally occurs at the same position in another VHH domain. Thus, any one or more substitutions, deletions or insertions, or any combination thereof, that either improve the properties of the nanobody of the disclosure or that at least do not detract too much from the desired properties or from the balance or combination of desired properties of the nanobody of the disclosure (i.e., to the extent that the nanobody is no longer suited for its intended use) are included within the scope of the disclosure. A skilled person will generally be able to determine and select suitable substitutions, deletions, insertions, additions, or suitable combinations of thereof, based on the disclosure herein and optionally after a limited degree of routine experimentation, which may, for example, involve introducing a limited number of possible substitutions and determining their influence on the properties of the nanobodies thus obtained.

For example, and depending on the host organism used to express the binding domain of the disclosure, preferably the nanobody, such deletions and/or substitutions may be designed in such a way that one or more sites for post-translational modification (such as one or more glycosylation sites) are removed, as will be within the ability of the person skilled in the art. Alternatively, substitutions or insertions may be designed so as to introduce one or more sites for attachment of functional groups, residues or moieties. Examples of modifications, as well as examples of amino acid residues within the binding domain sequence, preferably the nanobody sequence, that can be modified (i.e., either on the protein backbone but preferably on a side chain), methods and techniques that can be used to introduce such modifications and the potential uses and advantages of such modifications will be clear to the skilled person.

A particular type of modification may comprise the introduction of one or more detectable labels or other signal-generating groups or moieties, depending on the intended use of the labeled binding domain, in particular the nanobody. Suitable labels and techniques for attaching, using and detecting them will be clear to the skilled person, and, for example, include, but are not limited to, fluorescent labels, phosphorescent labels, chemiluminescent labels or bioluminescent labels, radio-isotopes, metals, metals chelates or metallic cations or other metals or metallic cations that are particularly suited for in vivo, in vitro or in situ diagnosis and imaging (including immunoassays known per se such as ELISA, RIA, EIA and other "sandwich assays," etc.), as well as chromophores and enzymes. Other suitable labels will be clear to the skilled person, and, for example, include moieties that can be detected using NMR or ESR spectroscopy. Yet another modification may comprise the introduction of a functional group that is one part of a specific binding pair, such as the biotin-(strept)avidin binding pair.

In a particular embodiment, the nanobody of the disclosure is bivalent and formed by bonding, chemically or by recombinant DNA techniques, together two monovalent single domain of heavy chains. In another particular embodiment, the nanobody of the disclosure is bi-specific and formed by bonding together two variable domains of heavy chains, each with a different specificity. Similarly, polypeptides comprising multivalent or multi-specific nanobodies are included here as non-limiting examples. Preferably, a monovalent nanobody of the disclosure is such that it will bind to an extracellular part, region, domain, loop or other extracellular epitope of a functional conformational state of a membrane protein, with a dissociation constant of less than 500 nM, preferably less than 200 nM, more preferably less than 10 nM, such as less than 500 pM. Alternatively, a monovalent nanobody of the disclosure is such that it will bind to an intracellular part, region, domain, loop or other intracellular epitope of a functional conformational state of a membrane protein, with an dissociation constant of less than 500 nM, preferably less than 200 nM, more preferably less than 10 nM, such as less than 500 pM. Also, according to this aspect, any multivalent or multispecific, as defined herein, nanobody of the disclosure may also be suitably directed against two or more different extracellular or intracellular parts, regions, domains, loops or other extracellular or intracellular epitopes on the same antigen, for example, against two different extracellular or intracellular loops or against two different extracellular or intracellular parts of the transmembrane domains. Such multivalent or multispecific nanobodies of the disclosure may also have (or be engineered and/or selected for) increased avidity and/or improved selectivity for the desired target protein, and/or for any other desired property or combination of desired properties that may be obtained by the use of such multivalent or multispecific nanobodies. In a particular embodiment, such multivalent or multispecific nanobodies of the disclosure may also have (or be engineered and/or selected for) improved efficacy in modulating signaling activity of a target protein.

Various methods may be used to determine specific binding between the binding domain and a target membrane protein, including, for example, enzyme linked immunosorbent assays (ELISA), flow cytometry, surface plasmon resonance assays, and the like, which are common practice in the art, for example, in discussed in Sambrook et al., 2001. Molecular Cloning, A Laboratory Manual. Third Edition. Cold Spring Harbor Laboratory Press, Cold Spring Harbor, N.Y. It will be appreciated that for this purpose often a unique label or tag will be used, such as a peptide label, a nucleic acid label, a chemical label, a fluorescent label, or a radio frequency tag.

It should be clear that membrane proteins, as used herein, are conformationally complex proteins that exhibit a spectrum functional behavior in response to natural and synthetic ligands. Thus, in a preferred embodiment, the binding domains, as described hereinbefore, are capable of stabilizing, or otherwise, increasing the stability of a particular functional conformational state, as defined herein, of a membrane protein, such as an active or an inactive state, etc. Preferably, the binding domain is capable of inducing the formation of a functional conformational state in a membrane protein upon binding the protein. Taking a GPCR as a non-limiting example, the functional conformation state can be a basal conformational state, an active conformational state or an inactive conformational state. Preferably, the membrane protein is stabilized in a drugable conformation.

The wording "inducing" or "forcing" or "locking" or "trapping" or "fixing" or "freezing" or "stabilizing," with respect to a functional conformational state of a membrane protein, as used herein, refers to the retaining or holding of a membrane protein in a subset of the possible conformations that it could otherwise assume, due to the effects of the interaction of the protein with the binding domain, according to the disclosure. Accordingly, a protein that is "conformationally trapped" or "conformationally fixed" or "conformationally locked" or "conformationally frozen," or in a "stabilized conformation," as used herein, is one that is held in a subset of the possible conformations that it could otherwise assume, due to the effects of the interaction of the protein with the binding domain, according to the disclosure. Within this context, a binding domain that specifically or selectively binds to a specific conformation or conformational state of a protein refers to a binding domain that binds with a higher affinity to a protein in a subset of conformations or conformational states than to other conformations or conformational states that the protein may assume. One of skill in the art will recognize that binding domains that specifically or selectively bind to a specific conformation or conformational state of a protein will stabilize this specific conformation or conformational state.

It will be appreciated that having increased stability with respect to structure and/or a particular biological activity of a membrane protein may also be a guide to the stability to other denaturants or denaturing conditions including heat, a detergent, a chaotropic agent and an extreme pH. Accordingly, in a further embodiment, the binding domain, according to the disclosure, is capable of increasing the stability of a functional conformational state of a membrane protein under non-physiological conditions induced by dilution, concentration, buffer composition, heating, cooling, freezing, detergent, chaotropic agent, pH. In contrast to water-soluble proteins, thermodynamic studies of membrane protein folding and stability have proven to be extremely challenging, and complicated by the difficulty of finding conditions for reversible folding. Unfolding of helical membrane proteins induced by most methods, such as thermal and chemical approaches, is irreversible as reviewed by Stanley and Fleming (2008, Archives of Biochemistry and Biophysics 469:46). The term "thermostabilize," "thermostabilizing," "increasing the thermostability of," as used herein, therefore, refers to the functional rather than to the thermodynamic properties of a membrane protein and to the protein's resistance to irreversible denaturation induced by thermal and/or chemical approaches including, but not limited to, heating, cooling, freezing, chemical denaturants, pH, detergents, salts, additives, proteases or temperature. Irreversible denaturation leads to the irreversible unfolding of the functional conformations of the protein, loss of biological activity and aggregation of the denaturated protein. The term "(thermo)stabilize," "(thermo)stabilizing," "increasing the (thermo)stability of," as used herein, applies to membrane proteins embedded in lipid particles or lipid layers (for example, lipid monolayers, lipid bilayers, and the like) and to membrane proteins that have been solubilized in detergent.

Thus, in another preferred embodiment, the binding domain, according to the disclosure, is capable of increasing the thermostability of a functional conformational state of a membrane protein when co-expressed in a host cell. In relation to an increased stability to heat, this can be readily determined by measuring ligand binding or by using spectroscopic methods such as fluorescence, CD or light scattering that are sensitive to unfolding at increasing temperatures. It is preferred that the binding domain is capable of increasing the stability as measured by an increase in the thermal stability of a membrane protein in a functional conformational state with at least 2° C., at least 5° C., at least 8° C., and more preferably at least 10° C. or 15° C. or 20° C. In relation to an increased stability to a detergent or to a chaotrope, typically, the GPCR is incubated for a defined time in the presence of a test detergent or a test chaotropic agent and the stability is determined using, for example, ligand binding or a spectroscopic method, optionally at increasing temperatures as discussed above. According to still another preferred embodiment, the protein binding domain, according to the disclosure, is capable of increasing the stability to extreme pH of a functional conformational state of a membrane protein. In relation to an extreme of pH, a typical test pH would be chosen, for example, in the range 6 to 8, the range 5.5 to 8.5, the range 5 to 9, the range 4.5 to 9.5, more specifically in the range 4.5 to 5.5 (low pH) or in the range 8.5 to 9.5 (high pH).

According to yet another specific embodiment, the host cell of the disclosure is a glyco-engineered host cell. A "glyco-engineered host cell" refers to a host cell that has been genetically modified so that it expresses proteins with an altered N-glycan structure and/or O-glycan structure as compared to in a wild-type background. Typically, the naturally occurring modifications on glycoproteins have been altered by genetic engineering of enzymes involved in the glycosylation pathway. In general, sugar chains in N-linked glycosylation may be divided in three types: high-mannose (typically yeast), complex (typically mammalian) and hybrid type glycosylation. Besides that, a variety of O-glycan patterns exist, for example, with yeast oligomannosylglycans differing from mucin-type O-glycosylation in mammalian cells. The different types of N- and O-glycosylation are all well known to the skilled person and defined in the literature. Considerable effort has been directed towards the identification and optimization of strategies for the engineering of eukaryotic host cells that produce glycoproteins having a desired N- and/or O-glycosylation pattern and are known in the art (e.g., De Pourcq et al., 2010, Appl. Microbiol. Biotechnol. 87:1617). One non-limiting example of such a glyco-engineered expression system is described in patent application PCT/EP2009/060348 and relates to a eukaryotic host cell expressing both an endoglucosaminidase and a target protein, and wherein the expressed target proteins are characterized by a uniform N-glycosylation pattern (in particular one GlcNAc residue or a modification thereof such as GlcNAc modified with galactose or galactose and sialic acid). This can be, for example, particularly advantageous in crystallization studies of glycoproteins. Also encompassed are host cells genetically modified so that they express proteins or glycoproteins in which the glycosylation pattern is human-like or humanized (i.e., complex-type glycoproteins). This can be achieved by providing host cells, in particular lower eukaryotic host cells, having inactivated endogenous glycosylation enzymes and/or comprising at least one other exogenous nucleic acid sequence encoding at least one enzyme needed for complex glycosylation. Endogenous glycosylation enzymes, which could be inactivated, include the alpha-1,6-mannosyltransferase Och1p, Alg3p, alpha-1,3-mannosyltransferase of the Mnn1p family, beta-1,2-mannosyltransferases. Enzymes needed for complex glycosylation include, but are not limited to: N-acetylglucosaminyl transferase I, N-acetylglucosaminyl transferase II, mannosidase II, galactosyltransferase, fucosyltransferase and sialyltransferase, and enzymes that are involved in donor sugar nucleotide synthesis or transport. Still other glyco-engineered host cells, in particular yeast cells, that are envisaged here are characterized in that at least one enzyme involved in the production of high mannose structures (high mannose-type glycans) is not expressed. Enzymes involved in the production of high mannose structures typically are mannosyltransferases. In particular, alpha-1,6-mannosyltransferase Och1p, Alg3p, alpha-1,3-mannosyltransferase of the Mnn1p family, beta-1,2-mannosyltransferases may not be expressed. Thus, a host cell can additionally or alternatively be engineered to express one or more enzymes or enzyme activities, which enable the production of particular N-glycan structures at a high yield. Such an enzyme can be targeted to a host subcellular organelle in which the enzyme will have optimal activity, for example, by means of signal peptide not normally associated with the enzyme. It should be clear that the enzymes described herein and their activities are well-known in the art.

Still other preferred host cells are: eukaryotic host cells as described in patent application PCT/EP2011/059959, that have been engineered so to display increased membrane formation from which increased levels of proteins can be recovered; eukaryotic host cells overexpressing HAC1 as described in Guerfal et al., 2010, Microbial. Cell Factories, 9:49.

According to particularly envisaged embodiments, cell cultures of host cells of the disclosure are also provided, as well as membrane preparations derived thereof (including the target membrane protein attached to either the cell surface membrane or retained in another subcellular membrane compartment). Membrane preparations include membrane fragments as well as membrane-detergent extracts and can be prepared according to known techniques, for example, as reviewed in detail in Cooper, 2004, J. Mol. Recognit. 17:286, incorporated herein by reference. A membrane preparation is also meant to include any liposomal composition which may comprise natural or synthetic lipids or a combination thereof. Examples of membrane or liposomal compositions include, but are not limited to, organelles, membrane preparations, Virus Like Lipoparticles, lipid layers (bilayers and monolayers), lipid vesicles, high-density lipoparticles (e.g., nanodisks), and the like.

In another aspect, the disclosure provides vector constructs comprising an exogenous nucleic acid sequence, as described hereinbefore. Non-limiting examples are provided in the Example section.

Applications

In the disclosure, it was surprisingly found that co-expressing a membrane protein with a binding domain directed against the membrane protein results in an increased expression of the heterologously expressed membrane protein, which can be useful for many applications, as described further herein.

The host cells, or cell cultures or membrane preparations derived thereof, can be used to produce higher amounts of often poorly expressed and unstable target membrane proteins, optionally stabilized in a particular conformation, either at the cellular surface or in other cell compartments. As such, they are of immediate use as research tool for a wide range of functional and/or structural studies.

Accordingly, in a further aspect, the disclosure provides a method of producing or enhancing the production of a membrane protein in a host cell comprising the steps of:
   a. Providing a host cell, according to the disclosure, as described hereinbefore,
   b. Culturing the host cell under conditions suitable for co-expressing the membrane protein and the binding domain directed against the membrane protein.

In addition, also envisaged is a method of producing or enhancing the production of a membrane protein in a functional conformation in a host cell, the method comprising the steps of:
   a. Providing a host cell, according to the disclosure, as described hereinbefore,
   b. Culturing the host cell under conditions suitable for co-expressing the membrane protein and the binding domain directed against the membrane protein, in the presence of a ligand, such as an agonist, an antagonist, an inverse agonist.

According to specific embodiments of the above methods, the engineered host cells of the disclosure are cultured in the presence of a conformation-selective ligand, as defined herein. More specifically, the engineered host cells of the disclosure are cultured in the presence of an agonist, or an antagonist, or an inverse agonist, or a biased agonist; and/or a positive allosteric modulator, or a negative allosteric modulator, all as defined herein.

During or after the protein production in the host cells, the protein or proteins of interest can be recovered from the cells. Accordingly, the methods of protein production may, optionally, also comprising the step of isolating the expressed protein, either alone, or in complex with the binding domain and/or with a ligand and/or with one or more downstream interacting proteins. This typically involves recovery of the material wherein the protein(s) are present (e.g., a cell lysate or specific fraction thereof, the medium wherein the protein is secreted) and subsequent purification of the protein. Means that may be employed to this end are known to the skilled person and include specific antibodies, tags fused to the proteins, affinity purification columns, and the like. Advantageously, the binding domain itself may be a useful tool to purify the membrane protein in a functional conformational state, by fusing the membrane protein, and binding domain-coding genes to a different tag, which can then be used as consecutive handles for affinity chromatography. When using double affinity chromatography, only membrane proteins that interact specifically with the binding domain are isolated. Moreover, they are all forced in the same functional conformation, for example, and without the purpose of being limitative, an active or inactive state of a GPCR, depending on the agonistic or antagonistic characteristics of the binding domain, respectively.

Capturing and/or purifying the membrane protein in a particular conformation, either alone or in complex with a stabilizing binding domain, will allow subsequent crystallization of the complex with less engineering steps, resulting in crystals of the membrane protein in a functional conformational state. These structures are considered to be much more true to life than those in which part of the protein is mutated, deleted or replaced by other stabilizing protein structures. For example, almost all currently unravelled GPCR structures are fusion proteins of the GPCR, where intracellular loop 3 is exchanged for T4 lysozyme. This intervention can, however, cause conformational changes that are naturally not present. Therefore, it is of particular advantage to isolate and crystallize a membrane protein in a relevant conformation starting from a host cell culture co-expressing in high amounts the membrane protein and a stabilizing binding domain. All these advantages will make structure determination of membrane proteins much easier in the future.

In practice, methods and techniques for crystallography and structure determination are all well known by the skilled in the art. A variety of specialized crystallization methods for membrane proteins exist, and many of these are reviewed in Caffrey, 2003, J Struct. Biol. 142:108. In general terms, the methods are lipid-based methods that include adding lipid to the membrane protein-binding domain complex prior to crystallization. Many of these methods, including the lipidic cubic phase crystallization method and the bicelle crystallization method, exploit the spontaneous self-assembling properties of lipids and detergent as vesicles (vesicle-fusion method), discoidal micelles (bicelle method), and liquid crystals or mesophases (in meso or cubic-phase method). Lipidic cubic phases crystallization methods are described in, for example: Landau et al., 1996, Proc. Natl. Acad. Sci. 93:14532; Gouaux 1998, Structure 6:5; Rummel et al., 1998, J. Struct. Biol. 121:82; Nollert et al., 2004, Methods 34:348, which publications are incorporated by reference for disclosure of those methods. Bicelle crystallization methods are described in, for example: Faham et al., 2005, Protein Sci. 14:836; Faham et al., 2002, J Mol Biol. 316:1, which publications are incorporated by reference for disclosure of those methods.

It has been proven that protein binding domains, in particular VHHs or nanobodies, are very useful tools to improve the diffraction quality of protein crystals, in particular membrane protein crystals (e.g., GPCRs) so that the protein crystal structure can be solved (see, e.g., Rasmussen et al., 2011, Nature 469:175). The structure of a protein, in particular a membrane protein, includes the primary, secondary, tertiary and, if applicable, quaternary structure of the protein. "Solving the structure," as used herein, refers to determining the arrangement of atoms or the atomic coordinates of a protein, and is often done by a biophysical method, such as X-ray crystallography. The acquired structural information can then be used to help guide drug discovery.

Other applications are particularly envisaged by making direct use of the host cells or cell cultures, according to the disclosure, or by using membrane preparations derived thereof, which will be described further herein, including compound screening and immunizations.

In the process of compound screening, lead optimization and drug discovery, there is a requirement for faster, more effective, less expensive and especially information-rich screening assays that provide simultaneous information on various compound characteristics and their effects on various cellular pathways (i.e., efficacy, specificity, toxicity and drug metabolism). Thus, there is a need to quickly and inexpensively screen large numbers of compounds in order to identify new specific ligands of a protein of interest, preferably conformation-selective ligands, which may be potential new drug candidates. The disclosure solves this problem by providing host cells co-expressing at the cellular surface or in a particular cellular membrane fraction high levels of membrane proteins and binding domains directed against these membrane proteins. Preferably, the binding domains are conformation-selective binding domains that allosterically stabilize and/or lock the membrane protein in a functional conformational state, for example, Rasmussen et al., 2011, Nature 469:175. Such host cells, as well as host cell cultures or membrane preparations derived thereof, can then be used as immunogens or selection reagents for screening in a variety of contexts. Taking a GPCR as an example, a major advantage of the combined features of high expression levels and conformational stabilization by the binding domain is that the GPCR can be kept in a stabilized drugable conformation, for example, the active state conformation. This will allow to quickly and reliably screen for and differentiate between receptor agonists, inverse agonists, antagonists and/or modulators as well as inhibitors of GPCRs and GPCR-dependent pathways, so increasing the likelihood of identifying a ligand with the desired pharmacological properties. Even more preferably, the binding domains increase the thermostability of the membrane protein in a particular functional conformational state, thus protecting the membrane protein irreversible or thermal denaturation induced by the non-native conditions used in compound screening and drug discovery, without the need to rely on, for example, mutant GPCRs with increased stability. As such, screening performance for disease indications, associated with a particular functional conformer of a target membrane protein will be improved by making use of the host cells of the disclosure.

Thus, according to a preferred embodiment, the disclosure encompasses the use of the host cells, or host cell cultures, or membrane preparations derived thereof, according to the disclosure and as described hereinbefore, in screening and/or identification programs for conformation-selective binding partners of a membrane protein, which ultimately might lead to potential new drug candidates.

According to one embodiment, the disclosure envisages a method of identifying compounds capable of selectively binding to a functional conformational state of a membrane protein, the method comprising the steps of:

(i) Providing a host cell or host cell culture or membrane preparation derived thereof, according to the disclosure, harboring a membrane protein in a functional conformational state, and
(ii) Providing a test compound, and
(iii) Evaluating whether the test compound binds to the functional conformational state of the membrane protein, and
(iv) Selecting a compound that selectively binds to the functional conformational state of the membrane protein.

Specific preferences for the host cells, cultures and membrane preparations thereof are as defined above with respect to the first aspect of the disclosure.

Screening assays for drug discovery can be solid phase (e.g., beads, columns, slides, chips or plates) or solution phase assays, e.g., a binding assay, such as radioligand binding assays. In high-throughput assays, it is possible to screen up to several thousand different compounds in a single day in 96-, 384- or 1536-well formats. For example, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. It is possible to assay many plates per day; assay screens for up to about 6.000, 20.000, 50.000 or more different compounds are possible today. Preferably, a screening for membrane protein conformation-specific compounds will be performed starting from host cells, or host cell cultures, or membrane preparations derived thereof.

Various methods may be used to determine binding between the stabilized membrane protein and a test compound, including, for example, enzyme linked immunosorbent assays (ELISA), surface Plasmon resonance assays, chip-based assays, immunocytofluorescence, yeast two-hybrid technology and phage display, which are common practice in the art, for example, in Sambrook et al., 2001, Molecular Cloning, A Laboratory Manual. Third Edition. Cold Spring Harbor Laboratory Press, Cold Spring Harbor, N.Y. Other methods of detecting binding between a test compound and a membrane protein include ultrafiltration with ion spray mass spectroscopy/HPLC methods or other (bio)physical and analytical methods. Fluorescence Energy Resonance Transfer (FRET) methods, for example, well known to those skilled in the art, may also be used. It will be appreciated that a bound test compound can be detected using a unique label or tag associated with the compound, such as a peptide label, a nucleic acid label, a chemical label, a fluorescent label, or a radio frequency tag, as described further herein.

The compounds to be tested can be any small chemical compound, or a macromolecule, such as a protein, a sugar, nucleic acid or lipid. Typically, test compounds will be small chemical compounds, peptides, antibodies or fragments thereof. It will be appreciated that in some instances the test compound may be a library of test compounds. In particular, high-throughput screening assays for therapeutic compounds such as agonists, antagonists or inverse agonists and/or modulators form part of the disclosure. For high-throughput purposes, compound libraries or combinatorial libraries may be used such as allosteric compound libraries, peptide libraries, antibody libraries, fragment-based libraries, synthetic compound libraries, natural compound libraries, phage-display libraries and the like. Methodologies for preparing and screening such libraries are known to those of skill in the art.

The test compound may optionally be covalently or non-covalently linked to a detectable label. Suitable detectable labels and techniques for attaching, using and detecting them will be clear to the skilled person, and include, but are not limited to, any composition detectable by spectroscopic, photochemical, biochemical, immunochemical, electrical, optical or chemical means. Useful labels include magnetic beads (e.g., dynabeads), fluorescent dyes (e.g., all Alexa Fluor dyes, fluorescein isothiocyanate, Texas red, rhodamine, green fluorescent protein and the like), radiolabels (e.g., $^{3}H$, $^{125}I$, $^{35}S$, $^{14}C$, or $^{32}P$), enzymes (e.g., horse radish peroxidase, alkaline phosphatase), and colorimetric labels such as colloidal gold or colored glass or plastic (e.g., polystyrene, polypropylene, latex, etc.) beads. Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label. Other suitable detectable labels were described earlier within the context of the first aspect of the disclosure relating to a binding domain.

Thus, according to specific embodiments, the test compound as used in any of the above screening methods is selected from the group comprising a polypeptide, a peptide, a small molecule, a natural product, a peptidomimetic, a nucleic acid, a lipid, lipopeptide, a carbohydrate, an antibody or any fragment derived thereof, such as Fab, Fab' and F(ab')2, Fd, single-chain Fvs (scFv), single-chain antibodies, disulfide-linked Fvs (dsFv) and fragments comprising either a VL or VH domain, a heavy chain antibody (hcAb), a single domain antibody (sdAb), a minibody, the variable domain derived from camelid heavy chain antibodies (VHH or nanobody), the variable domain of the new antigen receptors derived from shark antibodies (VNAR), a protein scaffold including an alphabody, protein A, protein G, designed ankyrin-repeat domains (DARPins), fibronectin type III repeats, anticalins, knottins, engineered CH2 domains (nanoantibodies), as defined hereinbefore.

It may be desirable to identify and characterize natural or endogenous ligands of target membrane proteins. In particular, there is a need to "de-orphanise" GPCRs for which a natural activating ligand has not been identified. Such ligands may be recovered from biological samples such as blood or tissue extract or from libraries of ligands. Thus, according to a particular embodiment, the test compound, as used in any of the above screening methods, is provided as a biological sample. In particular, the sample can be any suitable sample taken from an individual. For example, the sample may be a body fluid sample such as blood, serum, plasma, spinal fluid.

In addition to establishing binding to a target membrane protein in a functional conformational state, it will also be desirable to determine the functional effect of a compound on the membrane protein. In particular, the host cells, host cell cultures or membrane preparations derived thereof, as described herein, can be used to screen for compounds and/or to validate hits or leads that modulate (increase or decrease) the biological activity of the membrane protein. The desired modulation in biological activity will depend on the target of choice. Taking a target GPCR as an example, the compounds may bind to the target GPCR resulting in the modulation (activation or inhibition) of the biological function of the GPCR, in particular the downstream receptor signaling. This modulation of GPCR signaling can occur ortho- or allosterically. The compounds may bind to the target GPCR so as to activate or increase receptor signaling; or alternatively, so as to decrease or inhibit receptor signaling. The compounds may also bind to the target GPCR in such a way that they block off the constitutive activity of the GPCR. The compounds may also bind to the target complex in such a way that they mediate allosteric modulation (e.g., bind to the GPCR at an allosteric site). In this way, the compounds may modulate the receptor function by binding to different regions in the GPCR (e.g., at allosteric sites). Reference is, for example, made to George et al., 2002, Nat. Rev. Drug Discov. 1:808; Kenakin 2002, Trends Pharmacol. Sci. 25:186; Rios et al., 2001, Pharmacol. Ther. 92:71. The compounds of the disclosure may also bind to the target GPCR in such a way that they prolong the duration of the GPCR-mediated signaling or that they enhance receptor signaling by increasing receptor-ligand affinity. Further, the compounds may also bind to the target GPCR in such a way that they inhibit or enhance the assembly of GPCR functional homomers or heteromers. The efficacy of the compounds and/or compositions comprising the same can be tested using any suitable in vitro assay, cell-based assay, in vivo assay and/or animal model known per se, or any combination thereof, depending on the specific disease or disorder involved.

It will be appreciated that the host cells and derivatives thereof, according to the disclosure, may be further engineered and are, thus, particularly useful tools for the development or improvement of cell-based assays. Cell-based assays are critical for assessing the mechanism of action of new biological targets and biological activity of chemical compounds. For example, without the purpose of being limitative, current cell-based assays for GPCRs include measures of pathway activation ($Ca^{2+}$ release, cAMP generation or transcriptional activity), measurements of protein trafficking by tagging GPCRs and downstream elements with GFP; and direct measures of interactions between proteins using Förster resonance energy transfer (FRET), bioluminescence resonance energy transfer (BRET) or yeast two-hybrid approaches.

Further, it may be particularly advantageous to immunize an animal with a host cell expressing a membrane protein and a binding domain, according to the disclosure, or a cell culture or membrane preparation derived thereof, in order to raise antibodies, preferably conformationally-selective antibodies against the target membrane protein. Thus, such immunization methods are also envisaged here. Methods for raising antibodies in vivo are known in the art, and are also described hereinbefore. Any suitable animal, e.g., a warm-blooded animal, in particular a mammal such as a rabbit, mouse, rat, camel, sheep, cow, shark, or pig or a bird such as a chicken or turkey, may be immunized using any of the techniques well known in the art suitable for generating an immune response. Following immunization, expression libraries encoding immunoglobulin genes, or portions thereof, expressed in bacteria, yeast, filamentous phages, ribosomes or ribosomal subunits or other display systems, can be made according to well-known techniques in the art. Further to that, the antibody libraries that are generated comprise a collection of suitable test compounds for use in any of the screening methods, as described hereinbefore. The antibodies that have been raised, as described hereinabove, may also be useful diagnostic tools to specifically detect membrane proteins in a particular conformational state, and, thus, also form part of the disclosure.

Still another aspect of the disclosure, relates to a kit comprising a host cell or a host cell culture or a membrane preparation, according to the disclosure. The kit may further comprise a combination of reagents such as buffers, molecular tags, vector constructs, reference sample material, as well as a suitable solid supports, and the like. Such a kit may be useful for any of the applications of the disclosure, as described herein. For example, the kit may comprise (a library of) test compounds useful for compound screening applications.

The following examples are intended to promote a further understanding of the disclosure. While the disclosure is described herein, with reference to illustrated embodiments, it should be understood that the disclosure is not limited hereto. Those having ordinary skill in the art and access to the teachings herein will recognize additional modifications and embodiments within the scope thereof. Therefore, the disclosure is limited only by the claims attached herein.

EXAMPLES

Co-Expression of a GPCR and an Anti-GPCR Nb in Yeast

Example 1: Anti-CXCR4 Nb Cloning and Expression in Pichia pastoris

Example 1.1: Pichia pastoris Cloning Procedure

Figure 2:
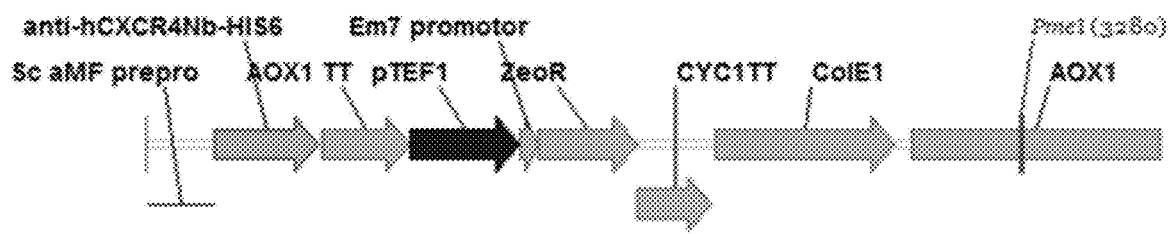
FIG. 2: Schematic overview of the pKai61-anti-hCXCR4Nb vector containing the anti-hCXCR4Nb gene under control of the AOX1 promoter. This vector was linearized with restriction enzyme PmeI to facilitate targeted integration in the AOX1 locus of the *Pichia* genome.

Four genes that code for Nanobodies directed against the extracellular side of the human CXCR4 receptor (FIG. 1; Table 1-2) were cloned into the pKai61 P. pastoris expression vector, in frame with a slightly modified version of the S. cerevisiae α-mating factor signal sequence. This signal sequence directs the proteins to the yeast secretory system and is further processed in the ER and the golgi and will be fully removed before secretion into the extracellular medium. In contrast to the wild-type prepro signal, this modified version does not contain sequences that code for the GluAla repeats (here the signal peptide is efficiently cleaved by the Kex2 endopeptidase without the need for this repeat). Expression in the secretory system is necessary for the Nanobodies to come into contact with their epitopes on the hCXCR4 GPCR upon correct integration into the membranes in later co-expression experiments (see Example 3). The encoded genes contain a C-terminal His6 tag, are N-terminally fused to the modified signal sequence of the S. cerevisiae α-mating factor and are under control of the methanol inducible AOX1 promoter. The plasmid contains a ZEOCIN® resistance marker for selection in bacterial as well as in yeast cells. The vectors were linearized in the AOX1 promoter (with PmeI) before transformation to P. pastoris to promote homologous recombination in the endogenous AOX1 locus for stable integration into the genome (FIG. 2).

Example 1.2: Anti-hCXCR4 Nanobody Expression in Pichia pastoris

Figure 3A:
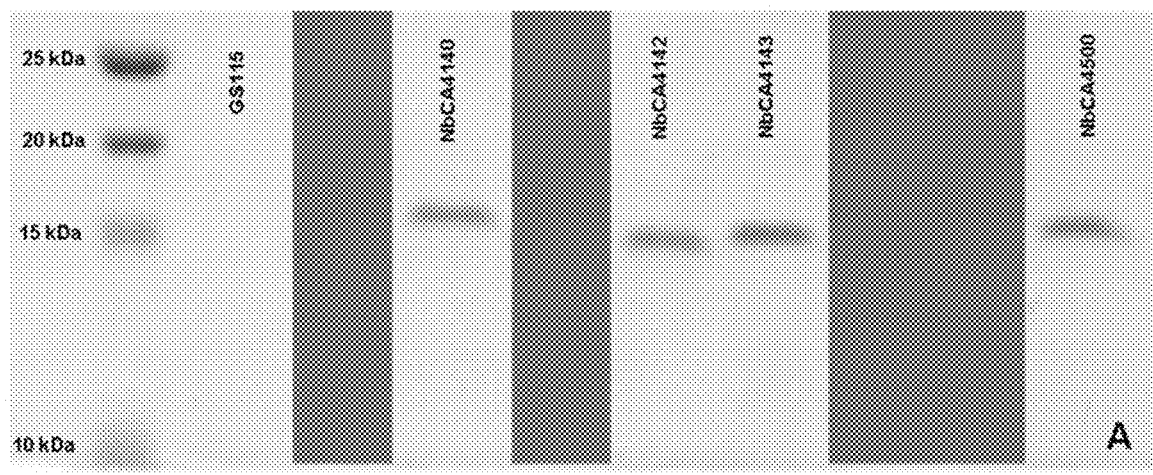
FIGS. 3A and 3B.
Figure 3B:
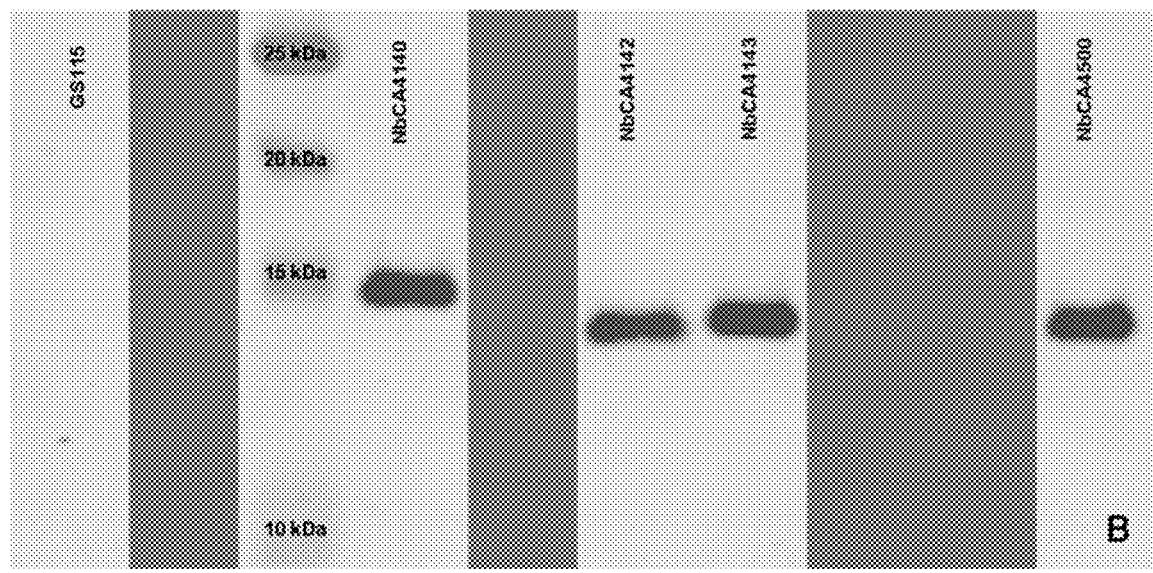

The four anti-hCXCR4 Nanobody expression vectors were transformed to the P. pastoris GS115 strain. Stable integrants were selected on YPD plates complemented with ZEOCIN® and confirmed by yeast colony PCR. These were grown and induced in buffered medium, as described in Material and Methods. A fraction of the extracellular growth medium was loaded on a 12% Tricine gel as such (complemented with 5× Laemmli dye and heated to 95° C. for 10 minutes) and stained with Coomassie Brilliant Blue (FIG. 3A) or blotted on a nitrocellulose membrane and subsequently developed with a primary mouse anti-His monoclonal antibody and a secondary Dylight (800 nm) goat anti-mouse IgG on a LI-COR odyssey system (FIG. 3B). Both the CBB-stained gel as the immunoblot showed clear protein bands of the correct size, indicating that each Nb is expressed and secreted by P. pastoris, without any signs of degradation.

Example 2: hCXCR4 Expression in Pichia pastoris

Figure 4A:
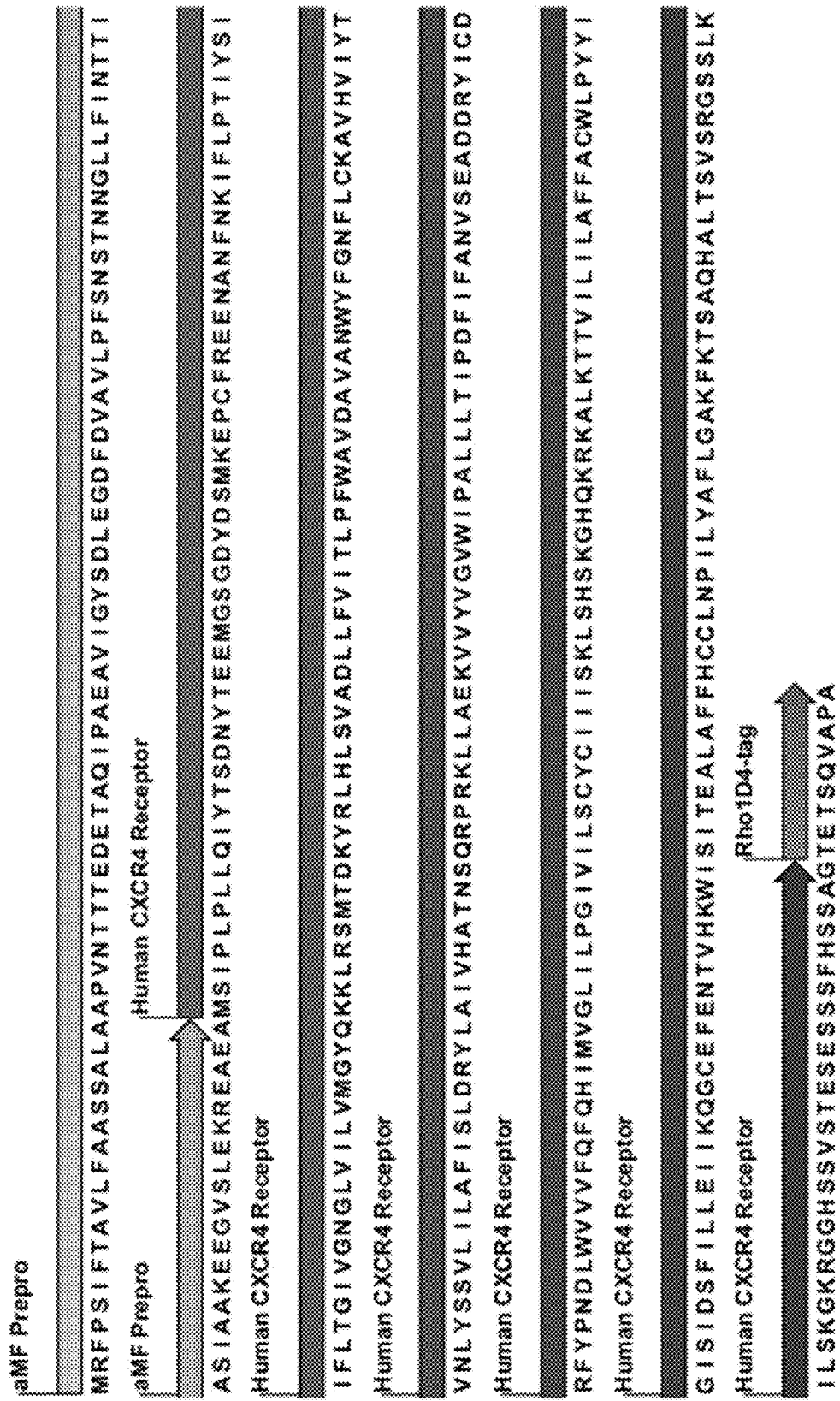
FIGS. 4A and 4B.
Figure 4B:
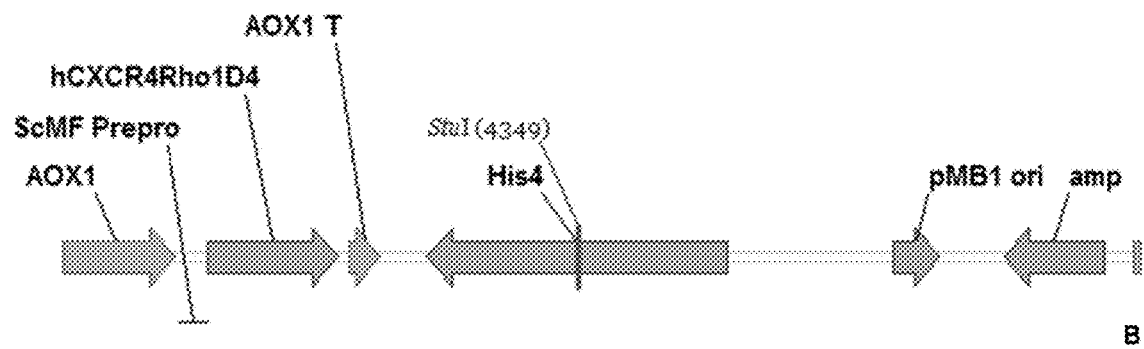

The full-length human CXCR4 gene was cloned into the pPIC92 P. pastoris expression vector. The encoded gene contains a C-terminal Rho1D4-tag (TETSQVAPA), is N-terminally fused to the signal sequence of the S. cerevisiae α-mating factor and the expression is under control of the methanol inducible AOX1 promoter. The plasmid contains a HIS4⁻ selection marker for selection in HIS4⁻ P. pastoris strains (e.g., GS115). The vector is linearized in the HIS4 marker (with StuI) before transformation to promote homologous recombination in the endogenous HIS4 locus for stable integration into the genome (FIG. 4).

Figure 5:
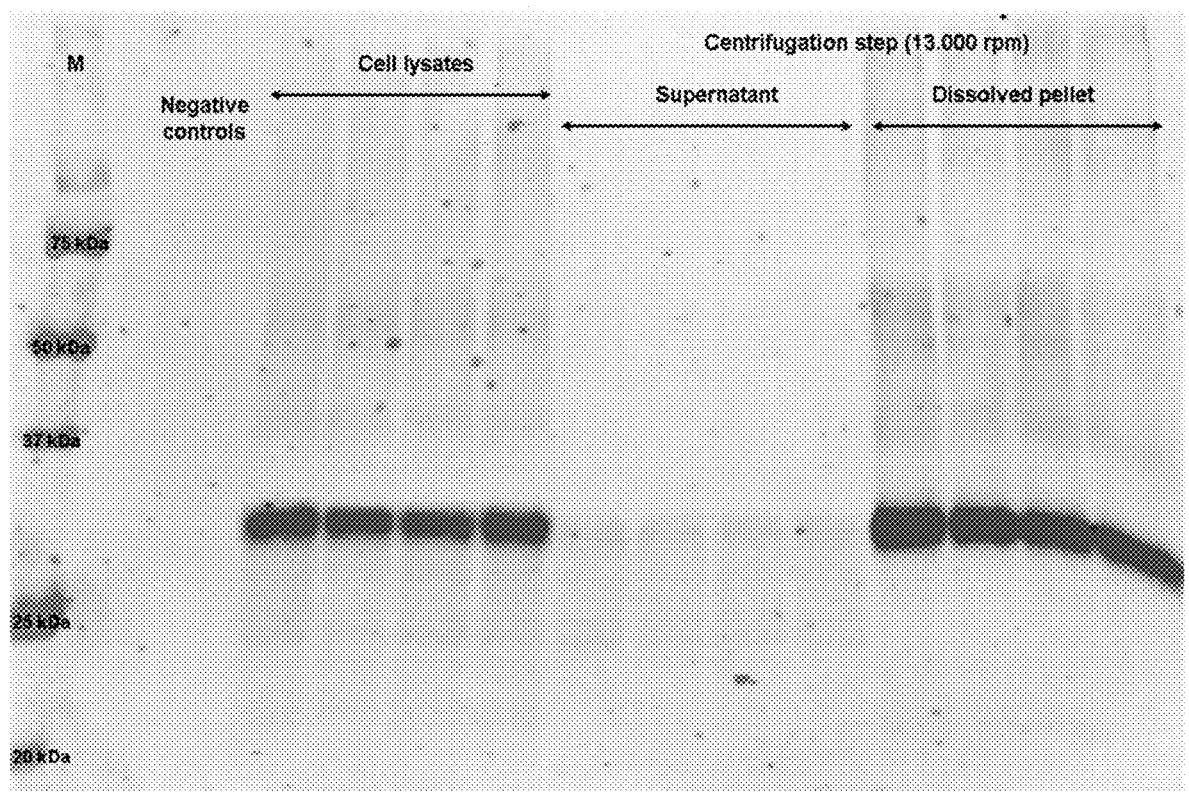
FIG. 5: Immunoblot analysis of hCXCR4Rho1D4 expressed in *P. pastoris*. M=All blue precision plus protein standards. Mouse anti-Rho1D4 antibody and secondary goat anti-mouse (800 nm) DyLight antibody was used for the detection of hCXCR4Rho1D4 on the Odyssey system.

Several P. pastoris GS115 clones, of which the stable insertion of the pPIC92hCXCR4Rho1D4 vector (FIG. 4) was confirmed, were selected to check hCXCR4 protein expression. The clones were grown and induced in buffered medium as described in Material and Methods. The cells were lysed and fractionated by centrifugation. Extracted proteins were tested for hCXCR4 expression by SDS-PAGE, followed by immunoblotting. Thereto, equal amounts of the different cell fractions were run on a 12% SDS-PAGE gel and blotted on a nitrocellulose membrane. The blot was developed with a primary mouse anti-Rho1D4 monoclonal antibody and a secondary Dylight (800 nm) goat anti-mouse IgG on a LI-COR odyssey system. FIG. 5 shows different cell fractions of four positive hCXCR4 expressing clones. A clear anti-Rho1D4 immunoreactive protein band is visible in the cell lysate fraction of all clones, with only faint signals at higher molecular weight, suggesting that the protein does not have the tendency to irreversibly aggregate during expression and extraction. The same cell lysate fractions are subsequently centrifuged at maximum speed in a table-top centrifuge. The same protein bands can be seen in the dissolved pellet fractions, while almost no signal can be detected in the supernatant. This indicates that the human CXCR4 receptor is indeed expressed in the membrane protein fractions. We used clone 1 for further experiments.

Example 3: hCXCR4-Nb Co-Expression in Pichia pastoris

Figure 6:
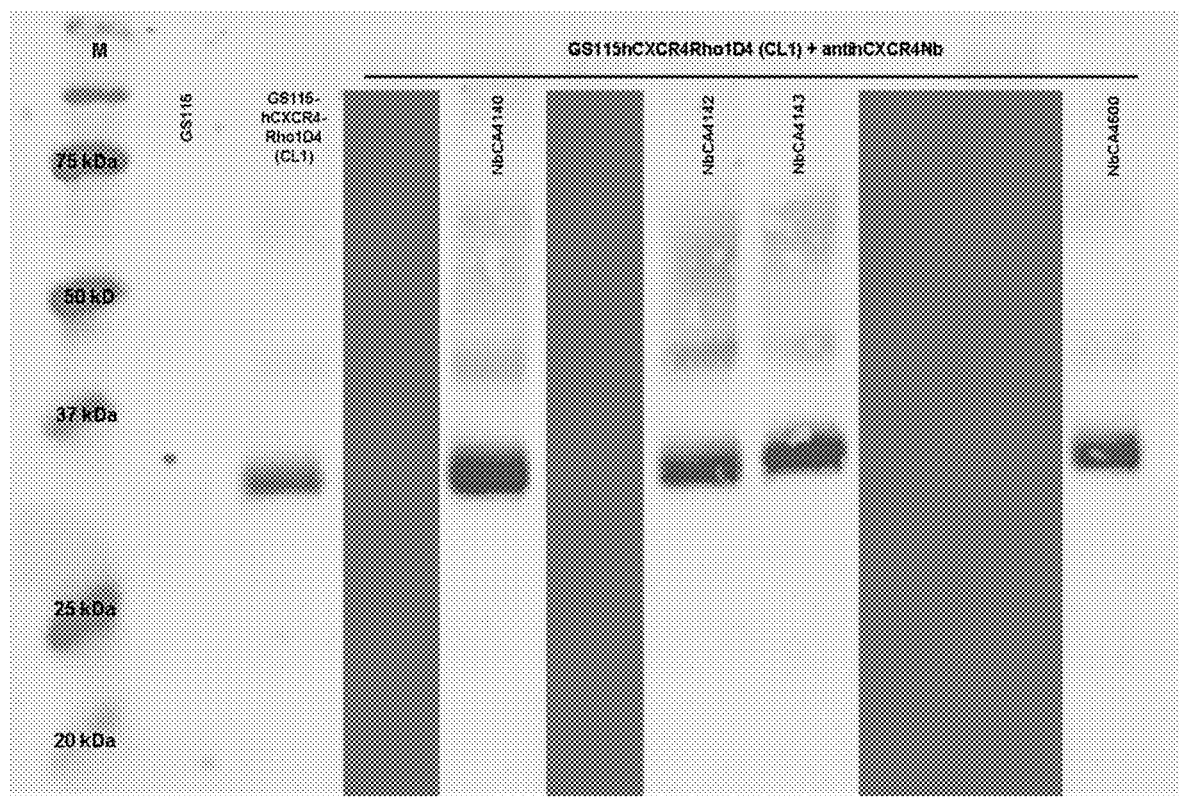
FIG. 6: Immunoblot analysis of hCXCR4Rho1D4 expressed in *P. pastoris* cells, expressing only hCXCR4Rho1D4 or co-expressing hCXCR4Rho1D4 and an anti-hCXCR4 Nanobody. M=All blue precision plus protein standards. Mouse anti-Rho1D4 antibody and secondary goat anti-mouse (800 nm) DyLight antibody was used for the detection of hCXCR4Rho1D4 on the Odyssey system.

An hCXCR4 expressing Pichia clone was transformed with the four linearized Nanobody expressing vectors as described before. Twenty-four positive clones (six per Nb) were analyzed for protein expression. Growth conditions and membrane protein sample preparations were done as previously described. Equal amounts of total membrane protein (determined by a BCA assay) of induced P. pastoris GS115 clones, expressing only the human CXCR4 receptor, or in combination with one of the anti-hCXCR4 Nanobodies, were run on a 12% SDS-PAGE gel and blotted on a nitrocellulose membrane. The blot was developed with a primary mouse anti-Rho1D4 monoclonal antibody and a secondary Dylight (800 nm) goat anti-mouse IgG on an LI-COR odyssey system. Protein expression of the highest hCXCR4 expressing clone of each hCXCR4-Nb combination is shown in FIG. 6. For each hCXCR4-Nb co-expressing clone we detect more (2 to 4 times) of the anti-Rho1D4 immunoreactive membrane protein band compared to the GS115hCXCR4 clone without Nb co-expression (except for Nb4500, here we only see a slight increase). The quantification was performed by the Odyssey software by measuring relative fluorescent signals (Table 3). Three out of four tested Nanobodies are able to significantly increase hCXCR4 protein expression in P. pastoris, as determined by quantifying the anti-Rho1D4 immunoreactive bands on western blot.

Figure 7A:
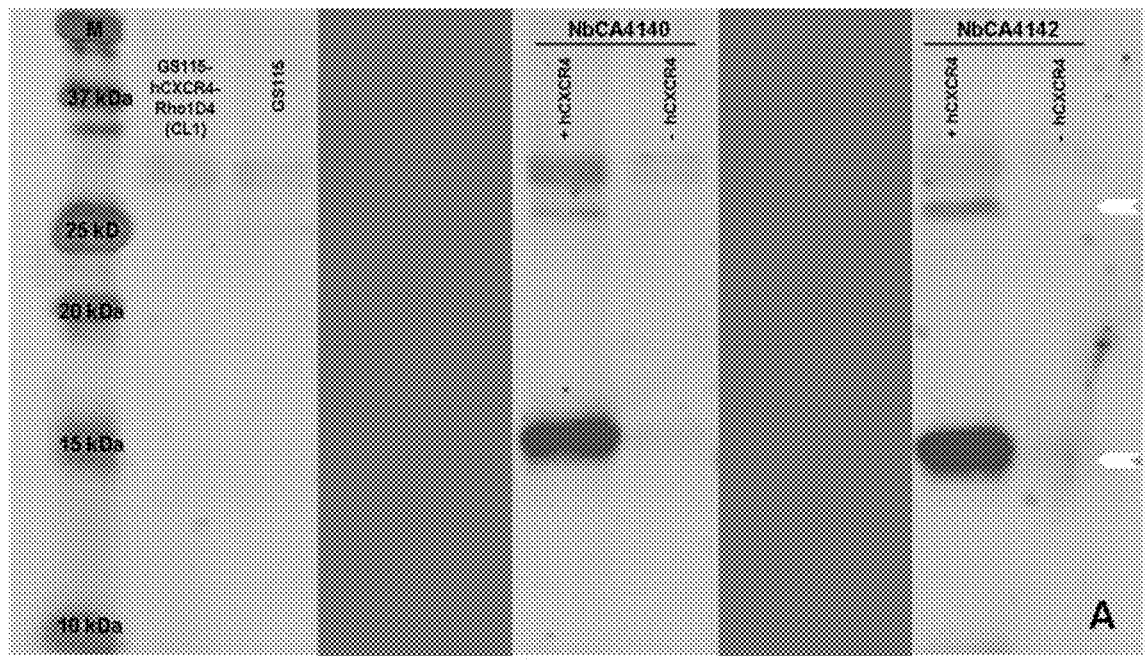
FIGS. 7A and 7B: Immunoblot analysis showing intracellular retention of the anti-hCXCR4 Nanobodies.
Figure 7B:
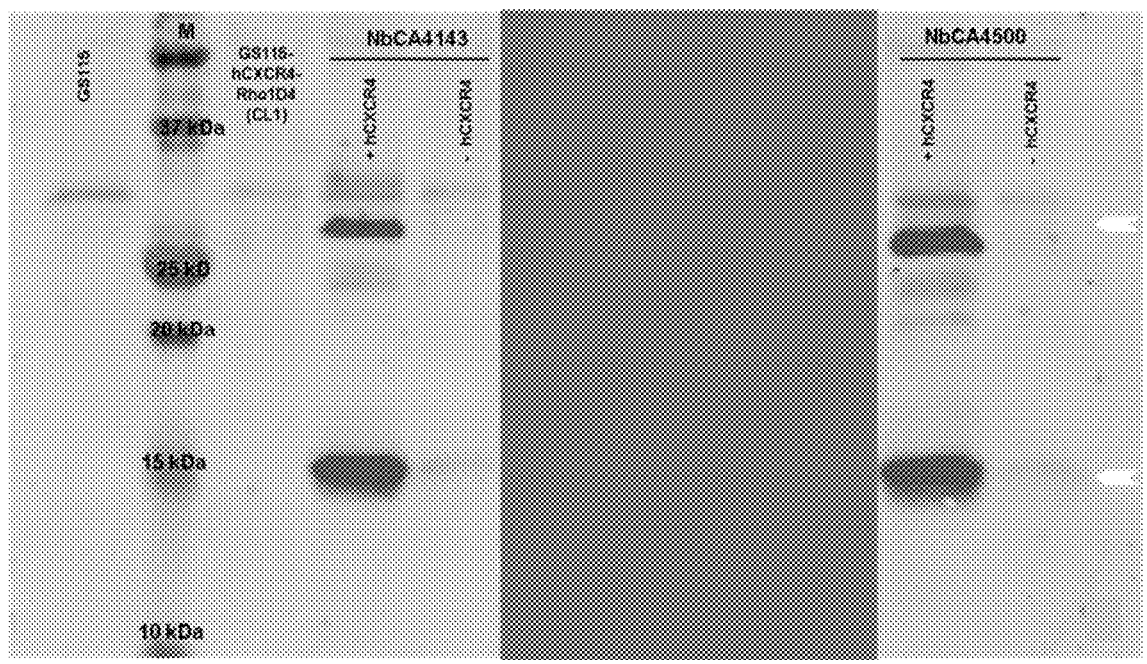

After induction, both the human CXCR4 membrane protein and the anti-hCXCR4 Nanobody are simultaneously expressed in the ER: the receptor is integrated in the ER membrane, while the Nbs will finally be secreted into the extracellular medium, unless they are able to bind their epitopes on the receptor somewhere along the secretory system. To check for possible in vivo binding, we first analyzed the intracellular retention of the Nanobodies in cells expressing Nbs alone or in combination with the human CXCR4 receptor (FIG. 7). Equal membrane protein fractions of induced *P. pastoris* GS115 clones, expressing only the human CXCR4 receptor or one of the four anti-hCXCR4 Nanobodies, or a combination, were run on a 15% SDS-PAGE gel and blotted on a nitrocellulose membrane. The blot was developed with a primary mouse anti-His monoclonal antibody and a secondary Dylight (800 nm) goat anti-mouse IgG on an LI-COR odyssey system. All Nanobodies are clearly retained in the membrane protein fractions of hCXCR4-Nb co-expressing clones (protein band around ±15 kDa), while almost no signal is detected in protein samples of clones lacking the hCXCR4 receptor. The extra band around 25 kDa represents a not fully processed form of the Nanobody, i.e., a form in which part of the signal peptide of the *S. cerevisiae* alpha-mating factor is yet uncleaved.

Figure 8:
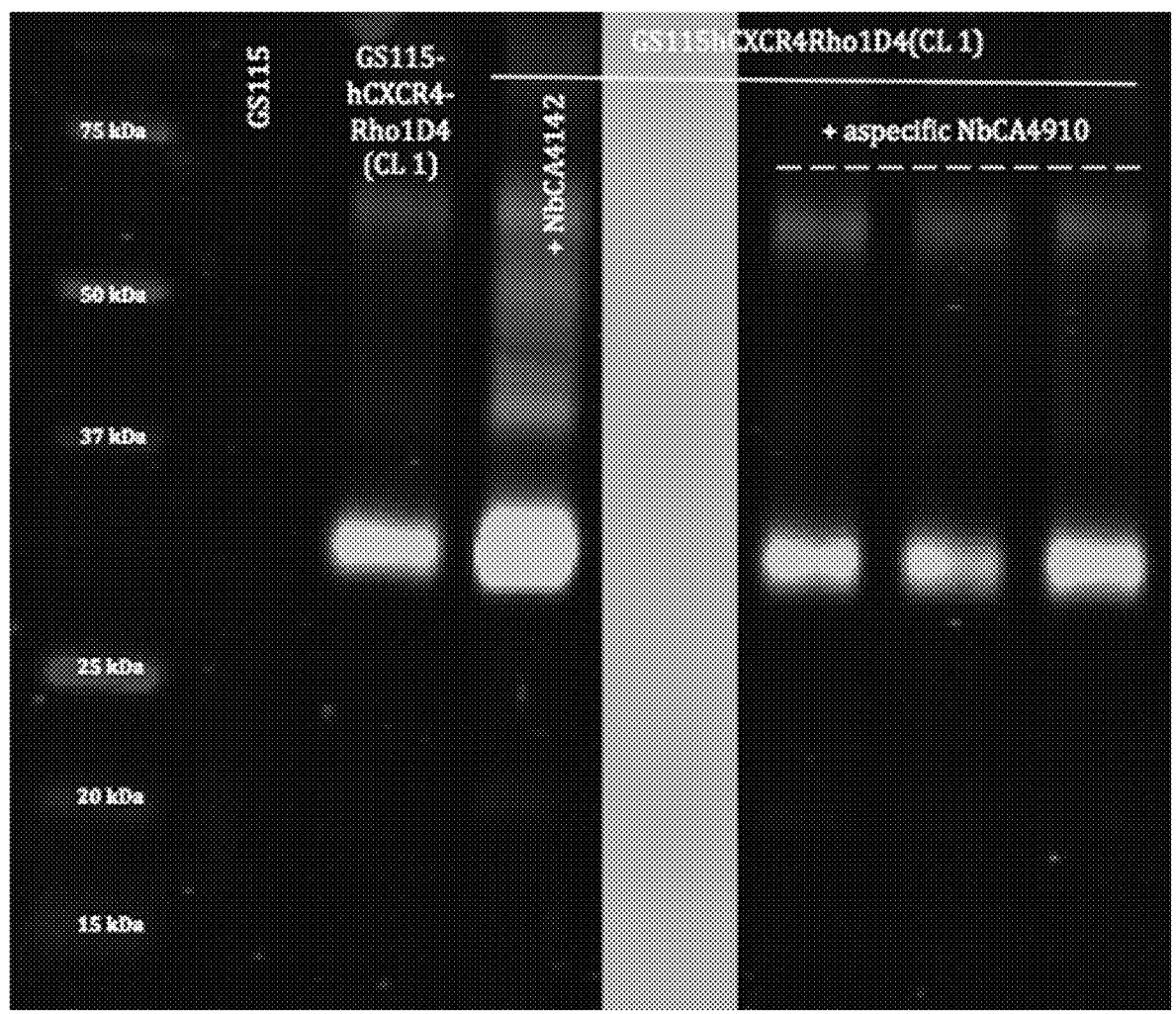
FIG. 8: Immunoblot analysis showing no increase in expression of the hCXCR4 receptor upon co-expression of a Nanobody that does not recognize the receptor (NbCA4910).M=All blue precision plus protein standards. Mouse anti-Rho1D4 antibody and secondary goat anti-mouse (800 nm) DyLight antibody was used for the detection of hCXCR4Rho1D4 on the Odyssey system.

In order to demonstrate that the increase in receptor expression is due to the interaction of a Nanobody specific for the receptor, a control experiment was performed using a Nanobody which does not recognize the hCXCR4 (Nanobody CA4910; amino acid sequence: SEQ ID NO:6; Nucleotide sequence: SEQ ID NO:24). An hCXCR4 expressing *Pichia* clone was transformed with the linearized Nanobody expressing vector as described before. Three positive clones were analyzed for protein expression. Growth conditions and membrane protein sample preparations were done as previously described. Equal amounts of total membrane protein (determined by a BCA assay) of induced *P. pastoris* GS115 clones, expressing only the human CXCR4 receptor, or in combination with a anti-hCXCR4 Nanobody (NbCA4142), or in combination with the negative control Nanobody (NbCA4910), were run on a 12% SDS-PAGE gel and blotted on a nitrocellulose membrane. The blot was developed with a primary mouse anti-Rho1D4 monoclonal antibody and a secondary Dylight (800 nm) goat anti-mouse IgG on an LI-COR odyssey system. Protein expression of the hCXCR4 is shown in FIG. 8. For the hCXCR4-specific Nb co-expressing clone we detect more of the anti-Rho1D4 immunoreactive membrane protein band compared to the GS115hCXCR4 clone without Nb co-expression. For the three clones, co-expressing the Nanobody that does not recognize the receptor, it is clear that there is no increase in the receptor expression. Exact quantification has been calculated by the Odyssey software by measuring relative fluorescent signals (Table 4). It can, thus, be concluded that the increase in receptor expression can be attributed to the Nanobody-specific interaction with the receptor.

Figure 9:
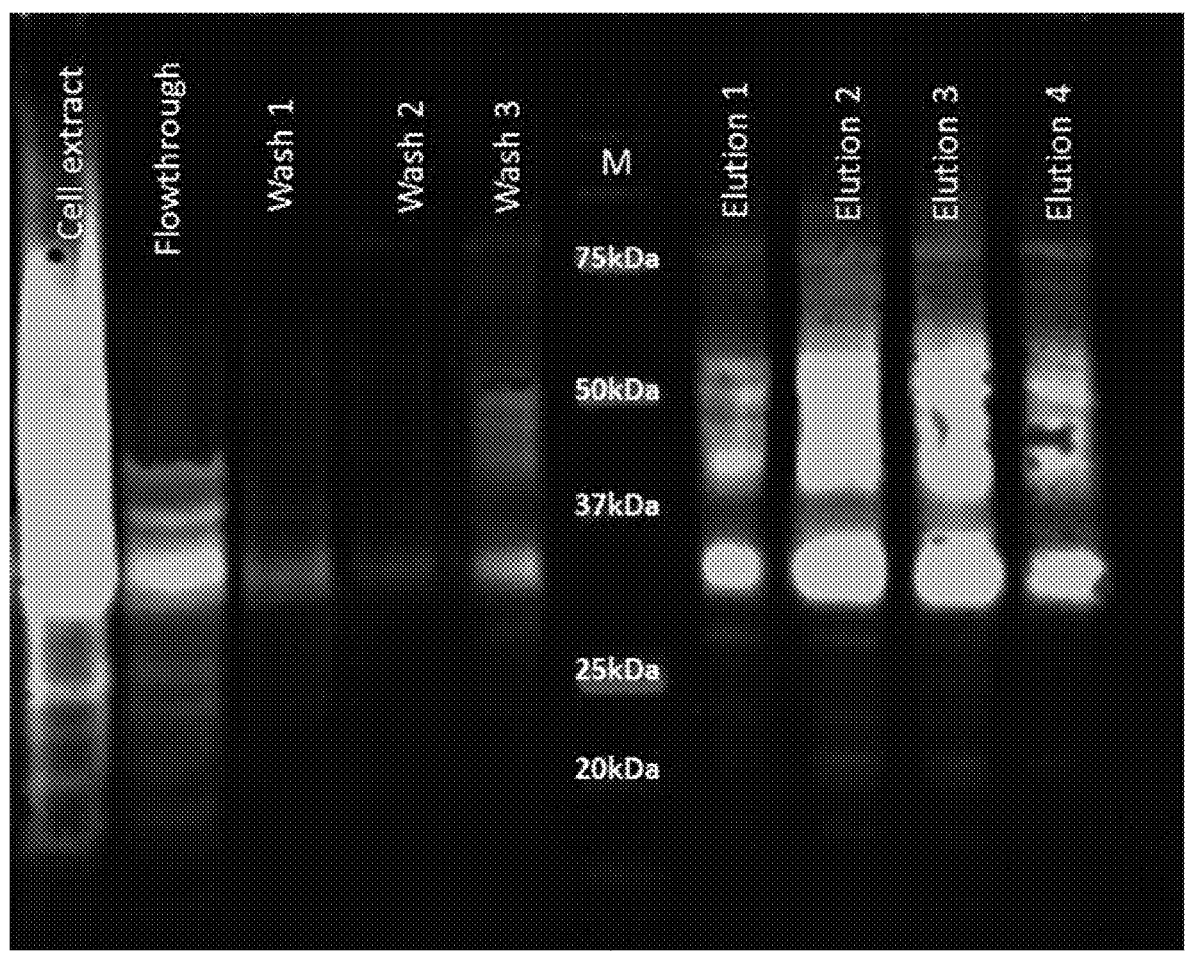
FIG. 9: Immunoblot analysis showing different purification steps of the hCXCR4 receptor using the Nanobody CA4142 as a purification handle. Respectively, the lanes contain cell extract, flowthrough, wash fraction 1, 2 and 3, M, elution 1 (100 mM Imidazole), elution 2, 3 and 4 (using 400 mM Imidazole). M=All blue precision plus protein standards. Mouse anti-Rho1D4 antibody and secondary goat anti-mouse (800 nm) DyLight antibody was used for the detection of the receptor on the Odyssey system.

Example 4: hCXCR4 Purification from *P. pastoris* Based on the Nanobody Interaction Because there is a strong interaction between the hCXCR4 receptor and NbCA4142, we could purify the membrane protein-Nanobody complex from a co-expressing clone, by $Ni^{2+}$ affinity chromatography for the hexaHis-tagged Nanobody. In this way we only purify the receptor fraction that is in a well-folded state, because the Nanobody can only bind the receptor when it is in its native fold. This step strongly increases homogeneity in a membrane protein sample which is useful, for example, for crystallization. Membrane protein preparation and purification was performed, as described in the methods section, and clearly resulted in strong retention of the receptor when brought on a $Ni^{2+}$ affinity column (FIG. 9). In case an even more pure sample is required, an extra step of affinity chromatography can be performed using an anti-Rho1D4 affinity matrix, which targets the hCXCR4 part of the complex.

Co-Expression of a GPCR and an Anti-GPCR Nb in Mammalian Cells

Figure 10:
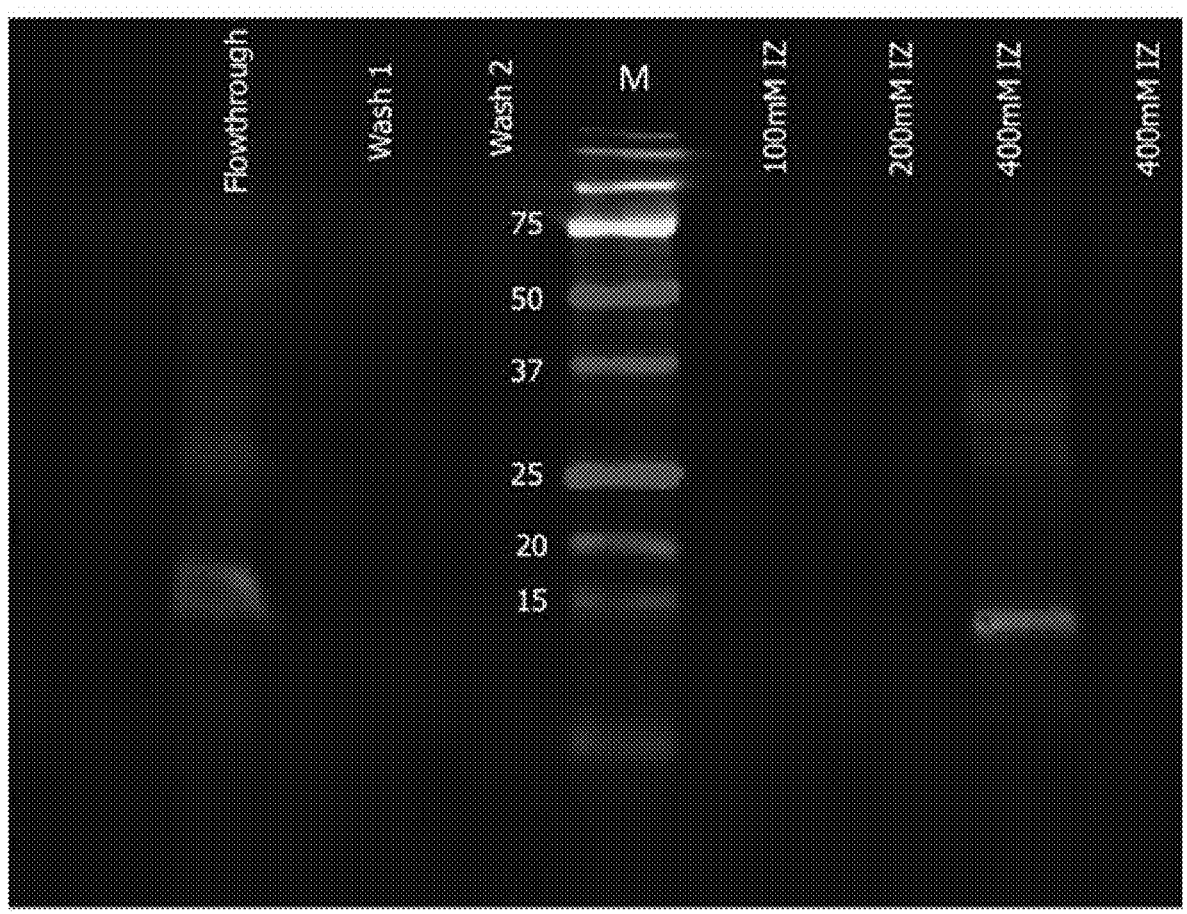
FIG. 10: Immunoblot analysis showing different purification steps of the b2AR using Nanobody CA2780 as a purification handle. Respectively, the lanes contain flowthrough, wash fraction 1 and 2, M, elution 1 (100 mM Imidazole), elution 2 (200 mM Imidazole), 3 and 4 (using 400 mM Imidazole). M=All blue precision plus protein standards. Mouse anti-Rho1D4 antibody and secondary goat anti-mouse (680 nm) DyLight antibody was used for the detection of the receptor, and 6×His Tag Antibody Dylight 800 antibody was used for the detection of the Nanobody on the Odyssey system.

Example 5: Co-Expression of β2AR-Nanobody in HEK293S GnT⁻ Cells and Purification of β2AR Based on the Nanobody Interaction The same technique as in Example 4 can be used using a Nanobody that binds an intracellular epitope of the membrane protein. Nanobody CA2780 (amino acid sequence: SEQ ID NO:5; Nucleotide sequence: SEQ ID NO:23) is an example of a Nanobody that binds an intracellular epitope of the β2-adrenergic receptor and that stabilizes the receptor in its active conformation (Rasmussen et al., 2011, Nature 469: 175). We transformed a HEK293 cell line that has a stable inducible β2AR expression with the pCAGGSNbCA2780-plasmid (see Material and Methods section) for transient expression. This Nanobody is not fused to a secretion signal and, therefore, resides in the cytosol upon expression, to allow interaction with the intracellular side of the membrane protein. Nanobody CA2780 has a hexaHis-tag and can, therefore, be purified using $Ni^{2+}$ affinity chromatography. Because there is a strong interaction between the β2AR receptor and NbCA2780 upon the addition of the agonist alprenolol hydrochloride, we could purify the membrane protein-Nanobody complex by $Ni^{2+}$ affinity chromatography for the hexaHis-tag on the Nanobody partner in the complex (FIG. 10). In this way we strongly enrich for the receptor fraction that is in a well-folded state, because the Nanobody can only bind the receptor when it is in its native fold. This step strongly increases homogeneity in a membrane protein sample going to f.e. crystallization trials. If necessary, a subsequent purification using anti-Rho1D4 affinity chromatography can further enrich the sample for the receptor.

Material and Methods
Materials

The *P. pastoris* GS115 strain was used for all yeast expression experiments. The pPIC92 vector was originally obtained from Invitrogen. The origin of the pKai61 vector is described in Schoonooghe et al., 2009, BMC Biotechnol. 9:70. MC1061 cells were used for the amplification of recombinant plasmid DNA.

The pCAGGS vector is described in Niwa et al., 1991, Gene, 108, 2: 193-199, and on the World Wide Web at addgene.org/vector-database/2042/, and was obtained from the BCCM plasmid collection. The HEK293S GnT⁻ cell line was obtained from the Prof. Dr. Prashen Chelikani (University of Manitoba, Winnipeg, Canada).

Media

Depending on the experimental settings, yeast strains were grown in YPD medium (10 g/L yeast extract, 20 g/L peptone, 20 g/L dextrose, ±20 g/L agar), BMY buffered complex medium (10 g/L yeast extract, 20 g/L peptone, 100 mM potassium phosphate buffer pH 6.0, 13.4 g/L YNB without amino acids, complemented with 1% glycerol (BMGY) or 1% methanol (BMMY)), Minimal medium without histidine (MM-HIS; 20 g/L agar, 13.4 g/L YNB without amino acids, 20 g/L dextrose, 0.79 g/L CSM-HIS).

Cloning
Construction of pKai61-antihCXCR4Nb Plasmid

All four Nb genes were PCR amplified (using Phusion polymerase) from the pMES4 vector in which they were initially cloned using primers NbXhoIFw 5'-GAAGAAGGGGTATCT<u>CTCGAG</u>AAAAGGCAGGT-GCAGCTGCAGG-3' (SEQ ID NO:26) and NbSpeIRev 5'-TCATGTCTAAGGCTA<u>ACTAGT</u>CTAGTGATGGTG-ATGG TGG-3' (SEQ ID NO:27). The Nanobody specific sequence is shown in italic; the 5' portion of each primer contains an XhoI and a SpeI RE recognition site, respectively, preceded by 15 bp homology to the pKai61 destination vector. The Fw primer also contains extra nucleotides to complete the signal sequence cleavage site. Each gel purified Nb PCR fragment was cloned into the linearized (XhoI and SpeI, fermentas; gel purified) pKai61 destination vector (in frame with the alpha-mating factor signal sequence from S. cerevisiae and under control of the methanol inducible AOX1 promoter; the vector also contains a ZEOCIN® resistance cassette for bacterial and yeast selection) using the commercial CloneEZ recombination kit, according to the manufacturer's instructions (Genscript). The reaction mixtures were transformed to E. coli MC1061 competent cells and ZEOCIN®-resistant clones were selected on LB Low Salt plates containing 50 μg/ml ZEOCIN®. Transformants were screened by colony PCR using the 5' (5'-GACTGGTTCCAATTGACAAGC-3'; SEQ ID NO:28) and 3' (5'-GCAAATGGCATTCTGACATCC-3'; SEQ ID NO:29) AOX1 promoter and terminator primers. All four final pKai61-antihCXCR4Nb plasmids were examined by restriction enzyme digestion and the inserts were sequence verified with the same 5' and 3' AOX1 primers.

Construction of pPIC92hCXCR4Rho1D4 Plasmid

The human CXCR4 gene (GenBank gene ID 7852, isoform a), fused to a sequence coding for the C-terminal Rho1D4 tag (TETSQVAPA; SEQ ID NO:25), was codon optimized for P. pastoris and synthetically synthesized by the Genscript corporation (cloned and delivered in the standard pUC57 vector). The gene was cloned into the pPIC92 P. pastoris expression vector, in frame with the α-mating factor signal sequence of S. cerevisiae, using conventional RE cloning (XhoI and NotI, fermentas). The ligation mixture was transformed to E. coli MC1061 competent cells and carbenicillin resistant clones were selected on LB Low Salt plates containing 50 μg/ml carbenicillin. Transformants were screened by colony PCR using the 5' and 3' AOX1 promoter and terminator primers. The final pPIC92hCXCR4Rho1D4 plasmid was examined by RE digestion and the hCXCR4Rho1D4 insert was sequence verified using the 5' and 3' AOX1 primers. The membrane protein gene is under control of the methanol inducible AOX1 promoter and the vector also contains a HIS4 marker for auxotrophic selection in the P. pastoris GS115 strain (HIS4⁻).

Yeast Transformation and Screening

The pPIC92hCXCR4Rho1D4 and the pKai61-antihCXCR4Nb plasmids were linearized (in the HIS4 resistance marker using StuI or in the AOX1 promoter region using PmeI, respectively) to increase transformation efficiency and to promote homologous recombination in the endogenous HIS4 or AOX1 locus for stable integration of the vector into the genome. Competent P. pastoris GS115 (HIS4⁻) cells were prepared and transformed by electroporation, according to the protocol from the Pichia Expression kit (Invitrogen Cat. No. K1710-01). Linearized plasmid (1 μg) was mixed with 80 μl competent cells in a 0.2 cm electroporation cuvette and the mixture was pulsed, according to the following settings: 25 pF; 200 Ω; 1.5 kV. Transformants were plated on selective medium (Minimal medium without histidine or YPD plates containing 100 μg/ml ZEOCIN®). Pichia colony PCR (i.e., yeast cells were pre-treated before the PCR reaction with a commercial zymolyase enzyme mixture and snap-frozen to weaken the cell wall) was performed using the 5' and 3' AOX1 primers to confirm the stable integration of the genes into the P. pastoris genome.

Yeast Cell Culture Conditions

Stable positive clones were typically grown in 2 ml (24-well format) or 12.5 ml (shake-flasks) BMGY medium for 48 hours (250 rpm; 28° C.). The cells were harvested by centrifugation and resuspended in the same amount of BMMY medium (1% methanol; 0.5% of methanol was added after 12 hours to maintain induction). After 24 hours the cells were harvested for membrane protein preparations (analysis of hCXCR4 expression and intracellular Nb retention) and the supernatant was used for analysis of extracellular protein expression on SDS-PAGE (Nanobodies).

Membrane Protein Preparations

The cell pellet corresponding to 1 ml of saturated yeast culture ($OD_{600}$ 60-80) was suspended in 1 ml of PBS+ Protease inhibitor (Roche). Together with 200 μl of acid washed glass beads, the samples were vortexed heavily at 4° C. for 2×5 minutes. Glass beads, cell debris and intact cells were removed by centrifugation at 2000 rpm (5 min; 4° C.). The supernatant was kept as such or was centrifuged for 45 minutes at 13,000 rpm in a desktop centrifuge at 4° C. The supernatant, cytosolic fraction was discarded and the pellet fraction was re-dissolved in the same amount of fresh PBS+PI by sonication until a homogenous sample was obtained.

Total membrane protein concentration was determined by the BCA protein assay kit (Pierce, Thermo Scientific).

SDS-PAGE and Western Blot Analysis

Protein samples were analyzed by SDS-poly-acrylamide gel electrophoresis, according to the Laemmli (Laemmli et al., 1970, Nature, 227:680) or the Tricine method (Schägger et al., 2006, Nat. Protoc. 1:16-22). Before loading on gel, the samples were mixed with 5× Laemmli (60 mM Tris-HCl pH 6.8; 2% SDS, 10% glycerol, 5% β-ME; 0.01% bromophenol blue) and heated for 10 minutes at 95° C. (only the ECM samples, not the membrane protein preparations). Prestained protein markers in the range of 10-250 kDa, Precision Plus protein standards (Bio-Rad), were used as molecular standards. Proteins in the gel were stained with Coomassie Brilliant Blue R-350 or they were electrotransferred at 10V, 100 mA/gel (semi-dry) for 90 minutes onto nitrocellulose membranes. The membranes were blocked overnight (4° C.) in PBS TWEEN® 20 (0.05%) containing 5% milk powder. They were then incubated for one hour at room temperature with a mouse anti-His (1/1000 of a 0.2 mg/ml stock in PBST; detection of Nanobodies) or a mouse anti-Rho1D4 (1/500 of a 5 mg/ml stock in PBST; detection of hCXCR4) monoclonal antibody, washed 3 times with PBST and then incubated for one hour with a secondary goat anti-mouse antibody (Dylight 800 nm). After the final washing steps, the membranes were scanned with a LI-COR Odyssey system. Analysis and quantification of the signals were done with the Odyssey software.

Construction of pCAGGSNbCA2780 Plasmid

The Nanobody gene was PCR amplified (using Phusion polymerase) from the pMES4 vector in which it was originally cloned using primers Nb80Fw Mc 5'-agtctg <u>CTCGAG</u>CCACCATGGAGGTGCAGCTGCAGG-3'

(SEQ ID NO:30) and Nb80Rev Mc 5'-cagact AGATCTctaGTGATGGTGATGATGATGTGCGGCCGC-TGAGGAGACGGTGA CCTGGGTCC-3' (SEQ ID NO:31). The Nanobody specific sequence is shown in italic; the 5' portion of each primer contains an XhoI and a BglII RE recognition site, respectively. Both primers also contain extra nucleotides to enable a restriction digest on the PCR product. The gel purified Nb PCR fragment was cloned into the linearized (XhoI (Fermentas), BglII (Promega); gel purified) pCAGGS destination vector, under control of the CMV immediate early promoter using T4 ligase (Fermentas); the vector also contains an ampicillin/carbenicillin resistance gene for bacterial selection. The reaction mixture was transformed to *E. coli* MC1061 competent cells and carbenicillin-resistant clones were selected on LB Low Salt plates containing 50 µg/ml carbenicillin. The final pCAGG-SNbCA2780 plasmid was examined by restriction enzyme digestion and the inserts were sequence verified with the traditional pCAGGS sequencing primers.

Transfection and Induction of NbCA2780 in HEK293S-β2AR

HEK293S-β2AR expressing cells (Chelikani et al., 2006, Protein Sci 15:1433) were grown to 60% to 80% confluence in a T175 Falcon and transfected with 1 µg pCAGG-SNbCA2780 using FuGeneHD Transfection Reagent (Promega). After 12 h, induction was performed using 1 µg/ml doxycyclin, 7.5 mM Na-butyrate and 1 µM alprenolol hydrochloride for 36 h.

Membrane Protein Isolation from *P. pastoris* for Purification

The cell pellet corresponding to 1 L of saturated yeast culture ($OD_{600}$ 60-80) was resuspended in a 1:1 (w/v) ratio of buffer A (1×PBS+Protease inhibitors). Together with 190 g of glass beads, the suspension was brought in the pre-cooled DYNO®-MILL mixing chamber and cells were crushed for 5 minutes. The lysate was centrifuged for 10 minutes at 2,000 rpm (Sorvall F10S-6X500Y rotor) at 4° C. to remove cell debris and intact cells. The supernatant was centrifuged for an hour at 13,000 rpm (Sorvall F10S-6X500Y rotor) at 4° C. to pellet the membrane proteins. The pellet was resuspended in 10 ml buffer A with 1% DDM (n-Dodecyl β-D-maltoside) and put on a rotor for three hours at 4° C. to allow membrane protein solubilization. After solubilization, the solution is centrifuged for one hour at 13,000 rpm (Sorvall SS-34 rotor) at 4° C. to remove unsolubilized membrane proteins.

Membrane Protein Isolation from HEK293S GnT⁻ for Purification

The cell pellet corresponding to one confluent T175 Falcon of transfected β2AR-expressing cells with NbCA2780 was resuspended in 4 mL lysis/solubilization buffer (1% NP40, 200 mM NaCl, 10 mM TrisHCl pH 7.5, 5 mM EDTA, 10% Glycerol, Protease Inhibitors, 1% DDM) and allowed to rotate for one hour at 4° C. The lysate is centrifuged at 2,000 rpm for 5 minutes to remove cell debris. The supernatant now contains the solubilized membrane proteins as well as the cytosol.

Membrane Protein Purification Using $Ni^{2+}$ Affinity Chromatography

The solubilized MP fraction is added to 0.5 ml of $Ni^{2+}$-loaded Chelating Sepharose Fast Flow matrix. Binding is performed overnight on a rotor at 4° C. Four consecutive washes are performed using 10 ml of buffer B (20 mM $NaH_2PO_4$, 500 mM NaCl, 20 mM Imidazole at pH 7.5). Then four consecutive elutions are done using increasing concentrations of buffer C (20 mM $NaH_2PO_4$, 20 mM NaCl, 400 mM Imidazole at pH 7.5). For the analysis, equal volumes were loaded on a 12% SDS-PAGE gel and Western blot was performed, as described before.

TABLE 1

List of nanobodies

| Nanobody reference number | SEQ ID NO | Amino acid sequence (including HIS tag) |
|---|---|---|
| CXCR4-specific nanobodies | | |
| CA4140 | 1 | QVQLQESGGGLVQPGGSLRLSCAASGSIFSINAMGWYR QAPGKQRELVAAITSGGSTNYADSVKGRFTISRDNAENT VYLQMNNLKPEDTAVYSCNAEGTSGSSRYRRRYEYWG KGTQVTVSSHHHHHH |
| CA4142 | 2 | QVQLQESGGGLVRTGGSLRLSCAGSGSFFSINPMGWYR QAPGQQRELVATITGSGSTNYADSVKGRFTISRDNAKNT LYLQMNSLKPEDTAVYYCNAGYFDRIGRRYDRWGQGT QVTVSSHHHHHH |
| CA4143 | 3 | QVQLQESGGGLYQPGGSLRLSCAASGFTFSSYAMSWVR QAPGKGLEWVSTINSGGRSANYADSVKGRLTISRDNAK NTLHLQMNSLKPEDTALYYCARPRSVSRNYVPLGYDYL GQGTQVTVSSHHHHHH |
| CA4500 | 4 | QVQLQESGGGLVQAGGSLRLSGAASGSTSGIIAMGWYR QAPGKQRELVARISSGGSTNYADSVKGRFTVSRDNAKN TVYLQMNSLKPEDTAVYYCNAVRRGYRNDYNSWGQG TQVTVSSHHHHHH |
| B2AR-specific nanobodies | | |
| CA2780 | 5 | MEVQLQESGGGLVQAGGSLRLSCAASGSIFSINTMGWY RQAPGKQRELVAAIHSGGSTNYANSVKGRFTISRDNAA NTVYLQMNSLKPEDTAVYYCNVKDYGAVLYEYDYWG QGTQVTVSSAAAHHHHHH |

TABLE 1-continued

List of nanobodies

| Nanobody reference number | SEQ ID NO | Amino acid sequence (including HIS tag) |
|---|---|---|
| control nanobody CA4910 | 6 | QVQLVESGGGLVQPGGSLRLSCAASGSFRSIVSMAWYR QAPGKQRELVASSNSGGSTNYADSVKGRFTISRDNAKN TVYLQMNSLKPEDTAVYWCNVQNRLPGFDAFSGRSIAE TYWGQGTQVTVSSAAAHHHHHH |
| CXCR4-specific nanobodies | | |
| CA4140 | 19 | caggtgcagctgcaggagtctggggggaggcttggtgcagcctgggggggtctctgagac tctcctgtgcagcctctggaagcatcttcagtatcaatgccatgggctggtaccgccaggc tccagggaagcagcgcgagttggtcgcagctattactagtggtggtagcacaaactatgc agactccgtaaagggccgattcaccatctccagagacaacgccgagaacacggtgtatc tgcaaatgaacaacctgaaacctgaggacacggccgtctattcatgtaacgctgaaggaa cgtcgggtagtagccggtatcgccgccggtatgagtactggggcaaggggacccaggt caccgtctcctcacaccaccatcaccatcac |
| CA4142 | 20 | caggtgcagctgcaggagtctggaggaggcttggtgcgcactgggggggtctagagac tctcctgtgaggctctggaagcttcttcagtatcaatcccatgggctggtaccgccaggct ccagggcagcagcgcgagttggtcgcaactattactggtagtggtagcacaaactatgca gactccgtgaagggccgattcaccatctccagagacaacgccaagaacacactgtatct gcaaatgaacagcctgaaacctgaggacacggccgtctattactgtaatgcaggatatttc gatcggattggtcggcggtatgaccgctggggccaggggacccaggtcaccgtctcctc acaccaccatcaccatcac |
| CA4143 | 21 | caggtgcagctgcaggagtctggaggaggcttggtgcagcctgggggggtctctgagac tctcctgtgcagcctctggattcaccttcagtagctatgccatgagctgggtccgccaggct ccaggaaaggggctcgagtgggtctcaactattaatagtggtggtcgtagcgcaaactat gcagactccgtgaagggccgactcaccatctccagagacaacgccaagaacacgctgc atctgcaaatgaacagcctgaaacctgaggacacggccctgtattactgtgcgagacccc gtagtgtaagtcgcaactatgttccactcggatacgactacttgggccaggggacccagg tcaccgtctcctcacaccaccatcaccatcactag |
| CA4500 | 22 | caggtgcagctgcaggagtctggaggaggcttggtgcaggctgggggggtctctgagac tctcctgtgagcctctggaagcacctccggtatcattgccatgggctggtaccgccagg ctccagggaagcagcgcgagttggtcgcacgtattagtagtggtagtagtacaaactatg cagactccgtgaagggccgattcaccgtctccagagacaacgccaagaacacagtgtat ctgcaaatgaacagcctgaaacctgaggacacggccgtctattactgtaatgcagtccgt cgaggttaccgtaacgactataactcctggggccaggggacccaggtcaccgtctcctc acaccaccatcaccatcactagactagt |
| β2AR specific nanobodies | | |
| CA2780 | 23 | atggaggtgcagctgcaggagtctggggggaggcttggtgcaggctgggggggtctctga gactctcctgtgcagcctctggaagcatcttcagtatcaataccatgggctggtaccgcca ggctccagggaagcagcgcgagttggtcgcagctattcatagtggtggtagcacaaact atgccaactccgtgaagggccgattcaccatctccagagacaatgccgcgaacacggtg tatctgcaaatgaacagcctgaaacctgaggacacggccgtctattactgtaatgtaaagg actacggggcggtcctatatgagtatgactactggggccaggggacccaggtcaccgtc tcctcagcggccgcacatcatcatcaccatcactag |
| control nanobody CA4910 | 24 | caggtgcagctggtggagtctggggggaggcttggtgcagcctgggggggtctctgagact ctcctgtgcagcctctggaagcttccgcagtatcgtgtctatggcctggtaccgccaggct ccagggaagcagcgcgagttggtcgcaagttctaatagtggggcagcacaaattatgc agactccgtgaagggccgattcaccatctccagagacaacgccaagaacacggtgtatc tgcaaatgaacagcctgaaacctgaggacacggccgtgtattggtgtaatgtccaaaacc gcctcccgggattcgacgcctttagtggcagatctatagcggagacctattggggccagg ggacccaggtcaccgtctcctcagcggccgcacatcatcatcaccatcac |

TABLE 2

CDRs of CXCR4-specific nanobodies

| Nanobody reference number | CDR1 (SEQ ID NO) | CDR2 (SEQ ID NO) | CDR3 (SEQ ID NO) |
|---|---|---|---|
| CA4140 | GSIFSINA (SEQ ID NO: 7) | AAITSGGSTNYADSVK (SEQ ID NO: 8) | NAEGTSGSSRYRRRYEY (SEQ ID NO: 9) |
| CA4142 | GSFFSINP (SEQ ID NO: 10) | ATITGSGSTNYADSVK (SEQ ID NO: 11) | NAGYFDRIGRRYDR (SEQ ID NO: 12) |
| CA4143 | GFTTFSSYA (SEQ ID NO: 13) | INSGGRSANYADSVK (SEQ ID NO: 14) | ARPRSVSRNYVPLGYDY (SEQ ID NO: 15) |
| CA4500 | GSTSGIIA (SEQ ID NO: 16) | ARISSGSSTNYADSVK (SEQ ID NO: 17) | NAVRRGYRNDYNS (SEQ ID NO: 18) |

TABLE 3

Relative hCXCR4 expression improvement factor for hCXCR4-Nb co-expressing strains versus the hCXCR4 expressing strain

| Sample | Fluorescent units | Blank corrected | Factor improvement |
|---|---|---|---|
| GS115 Negative control | 3.34 | 0 | — |
| GS115 + hCXCR4Rho1D4 (CL1) | 16.81 | 13.47 | 1.0 |
| GS115 + hCXCR4Rho1D4 (CL1) + NbCA4140 | 39.95 | 36.61 | 2.8 |
| GS115 + hCXCR4Rho1D4 (CL1) + NbCA4142 | 35.81 | 32.47 | 2.6 |
| GS115 + hCXCR4Rho1D4 (CL1) + NbCA4143 | 41.06 | 37.72 | 3.0 |
| GS115 + hCXCR4Rho1D4 (CL1) + NbCA4500 | 21.59 | 18.25 | 1.3 |

The shown relative fluorescent units are calculated by averaging data of two independent experiments. The "fluorescent unit" values are measured by the odyssey software.

TABLE 4

Relative hCXCR4 expression improvement factor for hCXCR4-Nb co-expressing strain versus the hCXCR4 expressing strain and the hCXCR4-Nb4910 co-expression strain

| Sample | Fluorescent units | Blank corrected | Factor improvement |
|---|---|---|---|
| GS115 Negative control | 2.41 | 0 | — |
| GS115 + hCXCR4Rho1D4 (CL1) | 18.45 | 16.04 | 1.0 |
| GS115 + hCXCR4Rho1D4 (CL1) + NbCA4142 | 32.76 | 30.35 | 1.9 |
| GS115 + hCXCR4Rho1D4 (CL1) + NbCA4910 cl1 | 8.97 | 6.56 | 0.4 |
| GS115 + hCXCR4Rho1D4 (CL1) + NbCA4910 cl2 | 20.30 | 17.89 | 1.1 |
| GS115 + hCXCR4Rho1D4 (CL1) + NbCA4910 cl3 | 21.90 | 19.49 | 1.2 |

The "fluorescent unit" values are measured by the odyssey software.

What is claimed is:

1. A recombinant cell comprising:
a first exogenous polynucleotide encoding a GPCR, and
a second exogenous polynucleotide encoding an immunoglobulin single variable domain that specifically binds an intracellular conformational epitope of the GPCR,
wherein the expression of each exogenous polynucleotide is under the control of a promoter;
wherein the amount of the GPCR in the recombinant cell is increased by at least two-fold as compared to an otherwise identical control cell not comprising the second exogenous polynucleotide;
wherein the immunoglobulin single variable domain was identified by a method comprising:
detecting specific binding of the immunoglobulin single variable domain to an intracellular conformational epitope of the GPCR;
co-expressing the immunoglobulin single variable domain with the GPCR in a host cell; and
detecting an increased amount of the GPCR by at least two-fold in the host cell as compared to an otherwise identical host cell not comprising the immunoglobulin single variable domain.

2. The recombinant cell of claim 1, wherein detecting specific binding of the immunoglobulin single variable domain to the GPCR comprises screening a library of immunoglobulin single variable domains to identify an immunoglobulin single variable domain that, when coexpressed with the GPCR, specifically binds to an intracellular conformational epitope in the GPCR, and increases the amount of the GPCR in the recombinant cell as compared to an otherwise identical cell not comprising the immunoglobulin single variable domain.

3. The recombinant cell of claim 2, wherein screening a library of immunoglobulin single variable domains to identify an immunoglobulin single variable domain comprises identifying an immunoglobulin single variable domain that increases the amount of the GPCR in the cell by at least two-fold as compared to an otherwise identical cell not comprising the immunoglobulin single variable domain.

4. The recombinant cell of claim 1, wherein said promoter is a constitutive promoter or an inducible promoter.

5. The recombinant cell of claim 1, wherein said GPCR and immunoglobulin single variable domain are co-expressed by the recombinant cell.

6. The recombinant cell of claim 1, wherein said GPCR and/or said immunoglobulin single variable domain are operably linked to one or more subcellular targeting sequences.

7. The recombinant cell of claim 1, wherein said immunoglobulin single variable domain comprises a peptide comprising four framework regions and three complementary determining regions, or any suitable fragment thereof.

8. The recombinant cell according to claim 7 wherein said immunoglobulin single variable domain is a nanobody.

9. The recombinant cell of claim 1, wherein said immunoglobulin single variable domain stabilizes said GPCR in a functional conformational state.

10. The recombinant cell of claim 1, wherein said recombinant cell is a eukaryotic cell.

11. The recombinant cell of claim 10 wherein said recombinant cell is a yeast selected from the group consisting of a *Pichia* strain, a *Komagataella* strain, a *Hansenula* strain, a *Yarrowia* strain, and a *Saccharomyces* strain.

12. The recombinant cell according to claim 10, wherein said recombinant cell is of human origin.

13. The recombinant cell of claim 10, wherein said recombinant cell is an Sf9 cell.

14. The recombinant cell of claim 1, wherein said recombinant cell is a glycoengineered cell.

15. The recombinant cell of claim 10, wherein the recombinant cell is a filamentous fungi selected from the group consisting of an *Aspergillus* strain, a *Penicillium* strain, and a *Hypocrea* strain.

* * * * *